US007029672B2

(12) United States Patent
Brancato et al.

(10) Patent No.: US 7,029,672 B2
(45) Date of Patent: Apr. 18, 2006

(54) USE OF QUINONE Q10 FOR THE TREATMENT OF OCULAR DISEASES

(75) Inventors: Rosario Brancato, Florence (IT); Giorgio Lenaz, Bologna (IT); Sergio Capaccioli, Florence (IT); Nicola Schiavone, Florence (IT)

(73) Assignee: Giuseppe Simonelli, Rome (IT)

( * ) Notice: Subject to any disclaimer, the term of this patent is extended or adjusted under 35 U.S.C. 154(b) by 289 days.

(21) Appl. No.: 10/323,820

(22) Filed: Dec. 20, 2002

(65) Prior Publication Data

US 2003/0118576 A1   Jun. 26, 2003

(30) Foreign Application Priority Data

Dec. 20, 2001  (IT)  .................. RM2001A0755

(51) Int. Cl.
*A61K 38/43*  (2006.01)
(52) U.S. Cl. ................................... 424/94.1
(58) Field of Classification Search .......... 424/94.1, 424/486; 514/690, 941
See application file for complete search history.

(56) References Cited

U.S. PATENT DOCUMENTS

| 4,871,742 | A | 10/1989 | Boone et al. |
|---|---|---|---|
| 6,403,116 | B1 | 6/2002 | Anderson et al. |
| 6,417,233 | B1 | 7/2002 | Sears et al. |
| 6,441,050 | B1 | 8/2002 | Chopra |
| 6,787,572 | B1 * | 9/2004 | Brancato et al. ............ 514/690 |
| 2002/0119936 | A1 | 8/2002 | Nyce |

FOREIGN PATENT DOCUMENTS

| IT | 1299578 | 3/2000 |
|---|---|---|
| WO | WO 96/17626 | 6/1996 |
| WO | WO 00/23069 | 4/2000 |
| WO | WO 00/57871 | 10/2000 |
| WO | WO 01/37851 | 5/2001 |
| WO | WO 01/37851 A2 | 5/2001 |
| WO | WO 01/37851 A3 | 5/2001 |
| WO | WO 02/17879 | 3/2002 |

OTHER PUBLICATIONS

Takahashi et al Biosis Abstract 1989:478937 "Effect of Coenzyme Q-10 on Hemodynamic response to ocular Timolol" J. Cardiovascular Pharm.(1989) vol. 14. No. 3, pp 462-46.*

Kuwayama: "Experimental Studies on Antioxidative Effect of Coenzyme $Q_{10}$ on the Retina," pp. 137-147; *Nagoya Med. J.* (1984) 29.

Rotig et al: "Quinone-responsive multiple respiratory-chain dysfunction due to widespread coenzyme $Q_{10}$ deficiency," pp. 391-395, *The Lancet*, vol. 356, Jul. 29, 2000.

Feher et al: IL Coenzima $Q_{10}$ Migliora La Funzione Visiva Nella Retinite Pigmentosa (Studio Preliminare), pp. 31-33, *Clin. Ocul. n.* Jan. 1996.

Benes: "Gradual Painless Visual Loss," pp. 47-85, *Visual and Auditory Challenges*, vol. 15, No. 1, Feb. 1999.

Blasi et al: "Does Coenzyme $Q_{10}$ Play A Role in Opposing Oxidative Stress in Patients with Age-Related Macular Degeneration?" pp. 51-54, *Ophthalmologica* 2001; 215-:51-54.

Florence: "The role of free radicals in disease," pp. 3-7, *The Ida Mann Lecture*. Presented at the $24^{th}$ Scientific Congress of The Royal Australian College of Ophthalmologists, Nov. 1992.

Kerrigan et al Archives of Ophthalmology vol. 115(8), Aug. 1997 pp. 1031-1035 TUNEL-Positive Ganglion Cells in Human Primary Open-angle Glaucoma.

Gross et al Survey of Ophthalmology, vol. 43 supp. 1, Jun. 1999 pp S162-S170 Retinal Ganglion Cell Dysfunction Induced by Hypoxia and Glutamate: Potential Neuroprotective Effects of β-Blockers.

(Continued)

*Primary Examiner*—Herbert J. Lilling
(74) *Attorney, Agent, or Firm*—Nixon & Vanderhye P.C.

(57) ABSTRACT

The present invention relates to the use of Coenzyme $Q_{10}$ or functionally equivalent derivatives thereof, through topical or systemic administration, for the prevention, the treatment and/or attenuation of degenerative ocular pathologies, said pathologies being of an heredofamilial, inflammatory, dysmetabolic, senile age-related nature, the degenerative process deriving from apoptotic events caused by hypoxia or other detrimental stimuli due to ischemia or to the lack of trophic factors.

13 Claims, 15 Drawing Sheets

OTHER PUBLICATIONS

Nickells Survey of Ophthalmology, vol. 43, supp 1, Jun. 1999 Apoptosis of Retinal Ganglion Cells in Glaucoma: An Update of the Molecular Pathways Involved in Cell Death.
Blankenberg et al Blood, vol. 89, No. 10 May 1997, pp. 3778-3786 Quantitative Analysis of Apoptotic Cell Death Using Proton Nuclear Magnetic Resonance Spectroscopy.

D.W. Nicholson, NATURE, vol. 407, Oct. 12, 2000 pp. 810-816.
A. Tempestini et al., European Journal of Ophthalmology, vol. 13, Suppl. 3, 2003 p. 1, 2, 6, 7, 8.
G. Carella European Journal of Ophthalmology vol. 13, Suppl. 3, 2003 pp. 51, 56, 58, 59, S10.

* cited by examiner

Untreated

UVC

AA

Ceramide

UVC + CoQ$_{10}$

AA + CoQ$_{10}$

Ceramide + CoQ$_{10}$

US 7,029,672 B2

USE OF QUINONE Q10 FOR THE TREATMENT OF OCULAR DISEASES

BACKGROUND OF THE INVENTION

1. Field of the Invention

The present invention relates to the use of Coenzyme $Q_{10}$ (or ubiquinone $Q_{10}$ or quinone $Q_{10}$, $CoQ_{10}$) or functionally equivalent derivatives thereof, for the prevention, the treatment and/or attenuation of degenerative ocular pathologies of a heredofamilial, inflammatory, dysmetabolic, senile age-related nature, the degenerative process deriving from apoptotic phenomena i.e. programmed cell death (PCD).

The present invention also envisages the systemic or topical administration of the Coenzyme $Q_{10}$ or functionally equivalent derivatives thereof.

2. Description of the Prior Art

Apoptosis, or programmed cell death (PCD), is involved in a large quantity of degenerative pathologies including pathologies of the eye's posterior chamber and of the perioptic area. Among these diseases there are heredofamilial, inflammatory, dysmetabolic and age-related macular and retinal degenerations e.g.: the glaucoma, the age-related macular degeneration, the retinitis pigmentosa, various heredofamilial maculopathies such as the Stargardt disease, the vitelliform macular cysts and the cones dystrophy, the diabetic retinopathy (exudative or proliferating), the hypertensive retinopathy, the ischemic opticopathy, the senile opacity of lenses, the cataract, the detachment of the retina, the uveitis, the retinoblastoma, the neuritis and the optical neuropathies of toxic, inflammatory and degenerative origin.

In all these pathologies the degeneration is due to the cell death through apoptosis.

The glaucoma may be taken as a paradigmatic example of such group of pathologies, in which apoptotic events play a major role, both for the pathogenetic mechanisms involved and for the spread of said disease. The glaucoma is an optical neuropathy, which determines a loss of ganglion cells, with a progressive loss of the visual field and of the visual function and subsequent excavation of the optic nerve head. The high intraocular pressure is a risk factor for the development of the disease and it is known that the decrease of the intraocular pressure protects the optic nerve from further damages.

In patients affected by glaucoma, the course of the disease is, usually, slow and irregular, with a marked interindividual variability. Although it does not seem that there is a direct correlation between the ganglion cells death and the progression of the visual field defects, it is believed that the cells loss precedes the onset of the visual field alterations. The progressive loss of the visual function was associated with several risk factors, such as the high intraocular pressure or the presence of a local or systemic deregulation of the haematic flow. Since experimental and clinic tests have demonstrated that ocular hypertension is a causal factor for the growth of the glaucomatous optical neuropathy, the universally accepted treatment is, at present, essentially limited to the reduction of the intraocular pressure, e.g., through medicaments having a diuretic effect, β-blocking medicaments, and others.

Said observations do not only concern human beings, but also mammals in general and, more particularly, house pets.

Recently, in vitro and in vivo studies on animal models, have suggested the possibility that a patient affected by glaucoma could benefit from a neuroprotective treatment, aimed at slowing down the progression of the death of ganglion cells (Nickells R. W. Apoptosis of retinal ganglion cells in glaucoma: an update of the molecular pathways involved in cell death. Surv Ophtalmol 1999; 43: S151–161). Furthermore, it is known that the highest part of retinal ganglion cells in glaucoma die through apoptosis (Kerrigan L. A., Zack D. J., Quigley H. A., et al. TUNEL-positive ganglion cells in human primary open-angle glaucoma. Arch Ophtalmol 1997; 115: 1031–1035) and that the hypoxia subsequent to ischemia is one of the ascertained causes of said cellular death (Gross R. L., Hensley S. H., Gao F., Wu S. M. Retinal ganglion cell dysfunction induced by hypoxia and glutamate: potential neuroprotective effects of beta-blockers. Surv Ophtalmol 1999, 43 Suppl:S162–70).

Although glaucoma has been herein used as a paradigmatic example, all the above mentioned degenerative pathologies share two common features, they damage the posterior part of the eye (i.e. retina and/or optic nerve) and they undergo several kind of apoptotic events in said tissues, said apoptotic events being caused by very different phenomena such as: ischemia, hypoxia/anoxia, lack of trophic factors, presence of free radicals.

Taking into account the common features shared by the above-mentioned pathologies, there is the need of providing means for the treatment, attenuation or prevention of all the above mentioned apoptotic events, hence, aiming at a neuroprotective activity in the posterior part of the eye.

PCT WO01/37851, in the name of the same Applicant of the present application, discloses the use of Coenzyme $Q_{10}$ in the prevention of PCD deriving from corneal photo refractive surgery treatments (anterior part of the eye) by means of excimer laser and exposure to ultraviolet rays.

The above-mentioned patent application teaches how to contend corneal cell apoptosis (anterior part of the eye) triggered by the creation of free radicals produced by electromagnetic radiations.

Coenzyme $Q_{10}$, or ubiquinone, is a coenzyme present in the cell on the mitochondrial internal membrane where its function, in association with a series of factors, in the electrons transport chain, which culminates with the production of energy in the form of adenosine triphosphate (ATP), is crucial. Moreover, Coenzyme $Q_{10}$ is an active scavenger of free radicals and its presence, associated exactly with said activity, has been detected also at the plasma membrane level. It has to be pointed out that the actual therapies of, e.g. glaucoma, are essentially limited to the reduction of the intraocular pressure and do not envisage a neuroprotective activity. To date, on the contrary, there is no knowledge concerning the activity of Coenzyme Q10 as a molecule that could have anti-apoptotic properties in pathological conditions wherein the apoptotic event can be also independent from the increase of free radicals. This is, in particular, the case of apoptosis due to ischemia, hypoxia/anoxia, lack of trophic factors. There is namely no news about the fact that Coenzyme $Q_{10}$ can function also in a different way with respect to its well-known antioxidant action. There is, therefore, the need for a neuroprotective therapy for the degenerative diseases of the posterior part of the eye, aimed at impeding, slowing or preventing the programmed cell death independently from the mechanisms entailing said PCD.

Said need derives from the observation that, among pathologies of the eye such as heredofamilial, inflammatory, dysmetabolic and age-related macular and retinal degenerations, the degenerative process due to apoptosis is not uniformly caused but is caused by an admixture of apoptotic phenomena triggered by different stimuli such as free radicals excess, ischemia, hypoxia/anoxia, lack of trophic factors. In all said pathologies the majority of the apoptotic events is not attributable to the presence of free radicals.

SUMMARY OF THE INVENTION

The present invention relies on the observation of two distinct, unexpected events.

The first is that the Coenzyme $Q_{10}$ unexpectedly accumulates in the retina also when administered topically on the anterior part of the eye.

The second, and more important is that the Coenzyme $Q_{10}$ extends its anti-apoptotic effects also to apoptotic events that are not caused by the generation of free radicals.

Therefore, the present invention provides means for the prevention, treatment and/or attenuation of apoptotic events in degenerative pathologies of the posterior part of the eye, independently from the mechanisms entailing said events (hence also apoptotic events not triggered by an excess of free radicals). Due to the variety of different pathways that can enhance an apoptotic response from the cell, and due to the fact that Coenzyme $Q_{10}$ is well known as a scavenger of free radicals, the anti-apoptotic effect of said molecule according to the invention was totally unexpected.

In the present application the surprising capability of Coenzyme Q10, in the prevention of apoptotic phenomena induced by three apoptotic stimuli that are known not to act through free radical generation and by UVC is demonstrated. Said stimuli, independent from free radicals generation, are:

1) Antimycin A, used as a model for the hypoxia caused apoptosis;
2) $C_2$-ceramide, which is a cell-permeable analogue of ceramide (a natural, lipidic, apoptotic messenger independent from free radicals) and;
3) Survival factor withdrawal by serum starvation, in which free radicals are not believed to cause the primary apoptotic insult.

The examples of the present application demonstrate that the above mentioned stimuli cause apoptotic events that do not involve the excess of free radicals and that Coenzyme Q10 has an anti-apoptotic effect also in said apoptotic events. What demonstrated in the present application concerning the general anti-apoptotic effect of Coenzyme Q10, is to be associated to the one newly herein disclosed for the first time, according to which, coenzyme $Q_{10}$ accumulates in the retinas and in the optic nerve of eyes treated with a preparation for topical use.

Hence, an object of the present invention is the use of the Coenzyme $Q_{10}$ or a functionally equivalent derivative thereof, as an active principle for the treatment, or for the manufacture of a medicament, for the prevention, treatment and/or attenuation of apoptotic events occurring in degenerative pathologies of the posterior part of the eye; the administration thereof being topical or systemic.

The apoptotic events prevented, treated or attenuated by the present invention are all apoptotic events causing ocular degenerative pathologies, more precisely affecting the posterior part of the eye. The meaning of "posterior part of the eye" according to the present invention is the retina and the optic nerve.

In particular, the use of the Coenzyme $Q_{10}$, or a functionally equivalent derivative thereof according to the present invention, is in the topical or systemic treatment, or in the manufacture of medicaments to use in said treatments, in order to prevent, attenuate or treat the apoptotic events induced by ischemia, hypoxia/anoxia, lack of trophic factors, excess of free radicals occurring in the posterior part of the eye. In particular, to treat the degenerative pathologies of the eye wherein said apoptotic events are directly involved in the degenerative process. More in particular, the degenerative pathologies according to the present invention are neurodegenerative pathologies.

More in particular, the use of Coenzyme $Q_{10}$, or a functionally equivalent derivative thereof according to the present invention, is for the treatment, or the manufacture of a medicament for the treatment of the apoptotic events of the pathologies of the retina and of the optic nerve, such as heredofamilial, inflammatory, dysmetabolic and age-related macular and retinal degenerations. Examples of said pathologies according to the invention are: the glaucoma, the age-related macular degeneration, the retinitis pigmentosa, various heredofamilial maculopathies such as the Stargardt disease, the vitelliform macular cysts and the cones dystrophy, the diabetic retinopathy (exudative or proliferating), the hypertensive retinopathy, the ischemic opticopathy, the senile opacity of lenses, the cataract, the detachment of the retina, the uveitis, the retinoblastoma, the neuritis and the optical neuropathies of toxic, inflammatory and degenerative origin, the pathogenetic mechanism of which also comprises an excess of programmed cell death (PCD) wherein free radicals are not involved.

According to the present invention, the Coenzyme $Q_{10}$ or a functionally equivalent derivative thereof, can be used for the above-mentioned treatments, or for the manufacture of the above mentioned medicaments, for human or for animal, use. Among animals, domestic animals and house pets are preferred.

The above-mentioned use of Coenzyme $Q_{10}$, or a functionally equivalent derivative thereof, can be performed through topic or systemic administration.

In a preferred embodiment of the invention, the Coenzyme $Q_{10}$, or functionally equivalent derivatives thereof, can be administered topically, in a medicament, in form of a collyrium. The formulations of a suitable collyrium comprising Coenzyme $Q_{10}$ are described in PCT WO01/37851.

The systemic administration of coenzyme $Q_{10}$, or functionally equivalent derivatives thereof, according to the present invention is either an oral or a parenteral administration, wherein Coenzyme $Q_{10}$, or its functionally equivalent derivative, is administered in a quantity higher than 20 mg per day, preferably in the range of 40, to 50, to 400 mg per day. Accordingly, Coenzyme $Q_{10}$, or a functionally equivalent derivative thereof, can be used for the manufacture of medicaments to be administered as described above.

Coenzyme $Q_{10}$, or functionally equivalent derivatives thereof, can be administered topically or systemically by all the ways known by the skilled person. By way of example, a systemic oral administration can be produced and administered to humans in a liquid or gel form as described in U.S. Pat. No. 6,441,050 and can be produced in a paste form that can be used as is or dried to form a powder and administered to animals in a liquid form or in baked or unbaked food products or in pills, tablets and capsules as described in U.S. Pat. No. 6,403,116.

For a systemic administration according to the present invention also the use of Coenzyme $Q_{10}$, or a functionally equivalent derivative thereof, for the manufacture of an injectable composition is envisaged. The systemic parenteral administration can be made with any injectable composition suitable for parenteral administration comprising Coenzyme $Q_{10}$ or its functionally equivalent derivative, sterile aqueous and non-aqueous injection solutions, suspensions and emulsions of the active compound, which preparations are preferably isotonic with the blood of the intended recipient as described in the U.S. Patent Application No. 20020119936. These preparations may also contain anti-oxidants, surfactants, buffers, bacteriostats, solutes that render the compositions isotonic with the blood of the intended recipient, and other formulation components known in the art. Extemporaneous injection solutions, suspensions and emulsions may be prepared from sterile powders, granules and tablets of the kind previously described.

According to the invention, the active compounds above described, may be administered once or several times a day. By functionally equivalent derivatives of coenzyme $Q_{10}$, all the possible derivatives of said molecule sharing the same functions of Coenzyme $Q_{10}$, e.g. ubiquinol, known in the art are defined in the present invention.

Figure 11A:
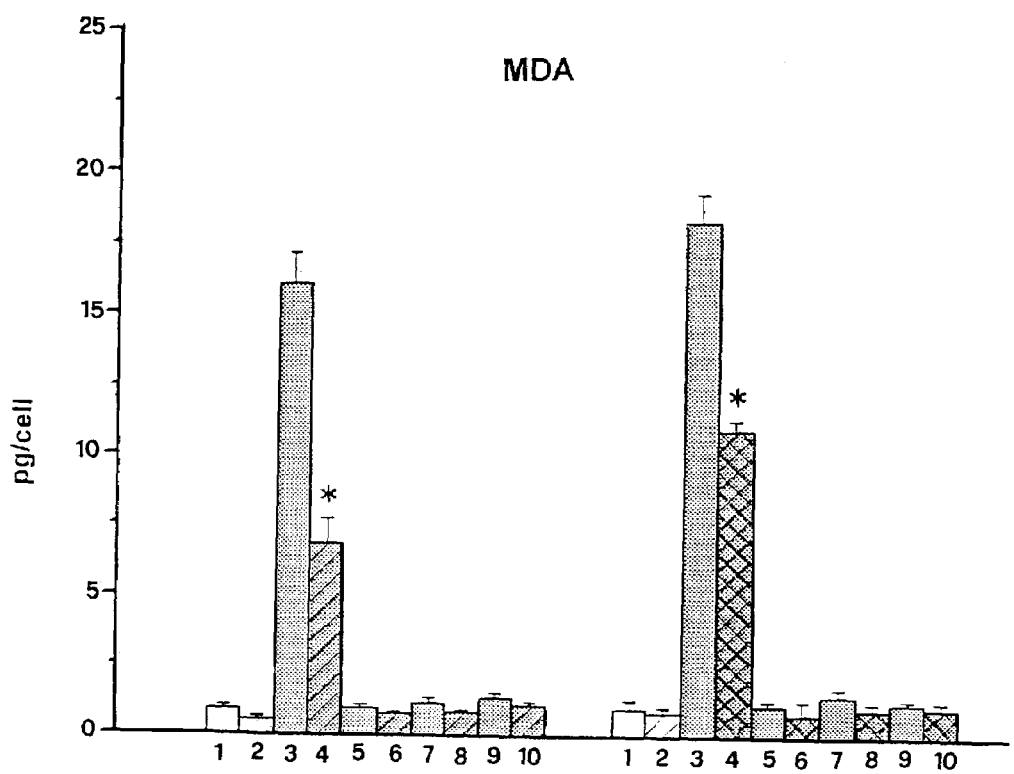
Figure 11B:
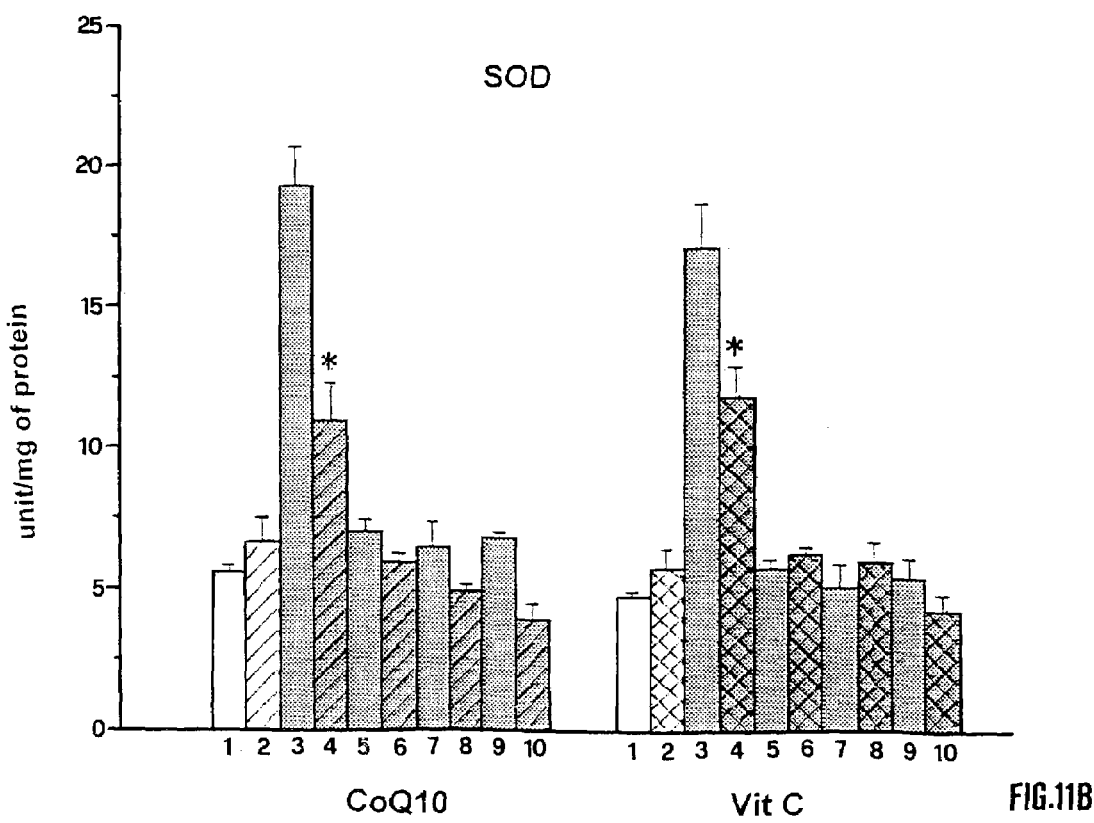

Each point is the mean±SE of 3 experiments. *p≦0.005 compared to Coenzyme $Q_{10}$ non-treated cells. ** p≦0.05 compared to Coenzyme $Q_{10}$ non-treated cells FIG. 11) Quantification of malonaldehyde (MDA) levels and SOD activity in RCE cells 24 hours after apoptotic stimulus with UVC at 254 nm (15 mJ/cm$^2$), Antimycin A (200 μM), ceramide (20 μM) or serum starvation, preceded or not by 2 hours treatment with 10 μM each Coenzyme $Q_{10}$ (left) or Vitamin C (right). RCE cells were: 1) unstimulated; 2) Coenzyme $Q_{10}$ or Vitamin C treated; 3) UVC irradiated; 4) Coenzyme $Q_{10}$ or Vitamin C treated and UVC irradiated; 5) Antimycin A stimulated; 6) Coenzyme $Q_{10}$ or Vitamin C treated and Antimycin A stimulated; 7) Ceramide stimulated; 8) Coenzyme $Q_{10}$ or Vitamin C treated and Ceramide stimulated; 9) Serum starved; 10) Coenzyme $Q_{10}$ or Vitamin C treated and serum starved. Each point was the mean±SE of 5 experiments, *p≦0.001 compared to Coenzyme $Q_{10}$ or Vitamin C untreated cells.

Figure 12:
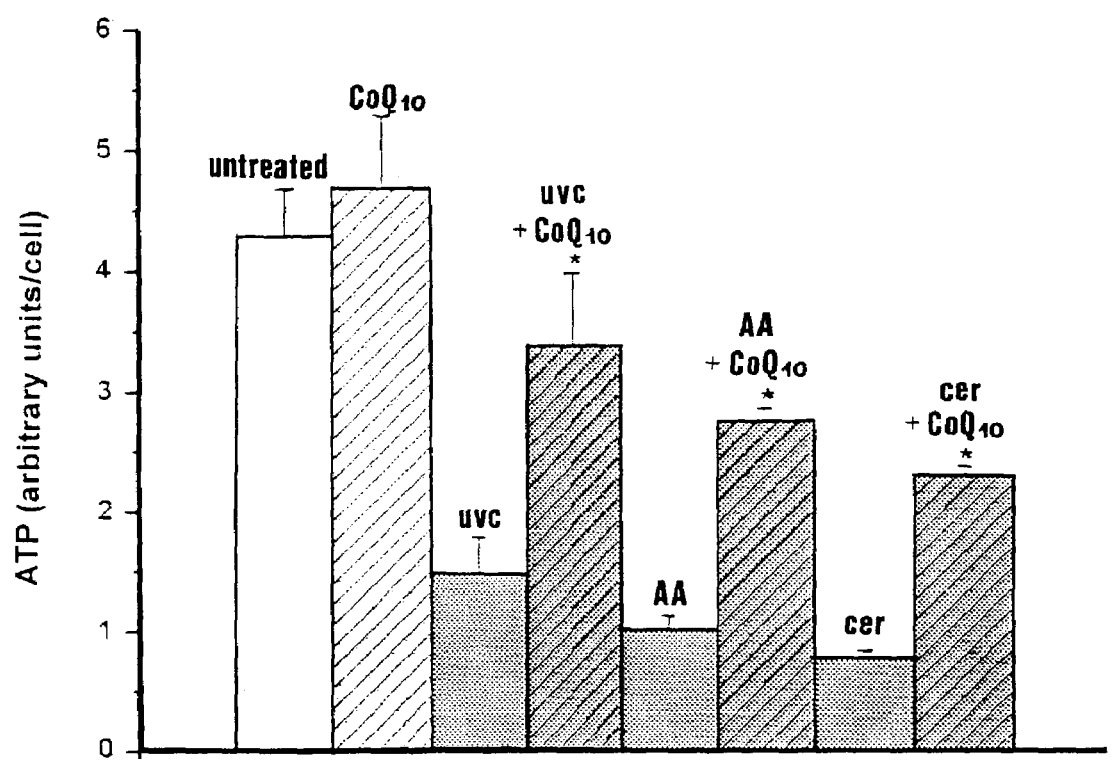
Figure 13A:
Figure 13B:
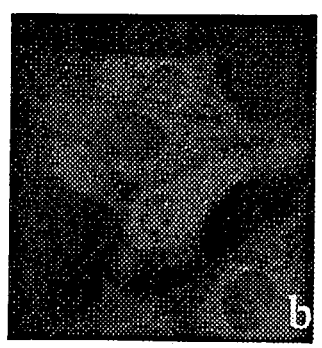
Figure 13C:
Figure 13D:
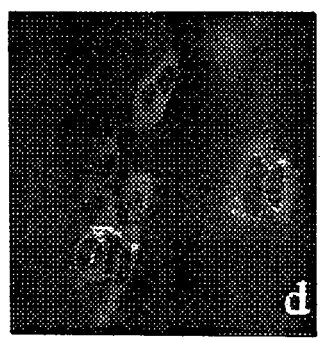
Figure 13E:
Figure 13E:
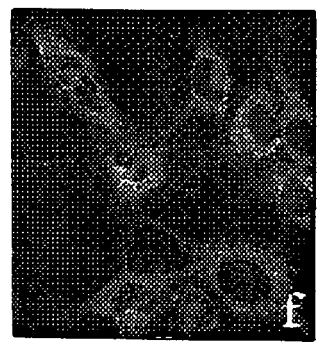
Figure 13G:

FIG. 12) Evaluation of ATP cellular levels in RCE cells 24 hours after application of apoptotic stimuli. Preparation of cell lysates is described in Material and Methods. Treatment with Coenzyme $Q_{10}$ significantly reduced the cellular ATP decrease. Each point is the mean±SE of 3 experiments. *p≦0.005 compared to Coenzyme $Q_{10}$ untreated cells.

FIG. 13) Detection of the mitochondrial membrane potential by double fluorescence JC-1 assay. Dual emission images (525 and 590 nm) represent the signal from monomeric (green) and J-aggregate (red) JC-1 fluorescence in RCE cells. (a) Untreated RCE cells show red stained mitochondria (large negative membrane potential). The mitochondria of RCE cells assayed 24 hours after apoptotic stimulus with (b) UVC irradiation; (d) 200 μM Antimycin A; or (f) 20 μM ceramide appeared uniformly green stained (lower membrane potential). Treatment with Coenzyme $Q_{10}$ significantly protected against loss of the mitochondrial membrane potential as evident from the reappearance of the red-stained mitochondria in RCE cells (c) Coenzyme $Q_{10}$ treated prior to UVC irradiation; (e) Coenzyme $Q_{10}$ treated prior to administration of Antimycin A; (g) Coenzyme $Q_{10}$ prior to administration of ceramide.

Figure 14:
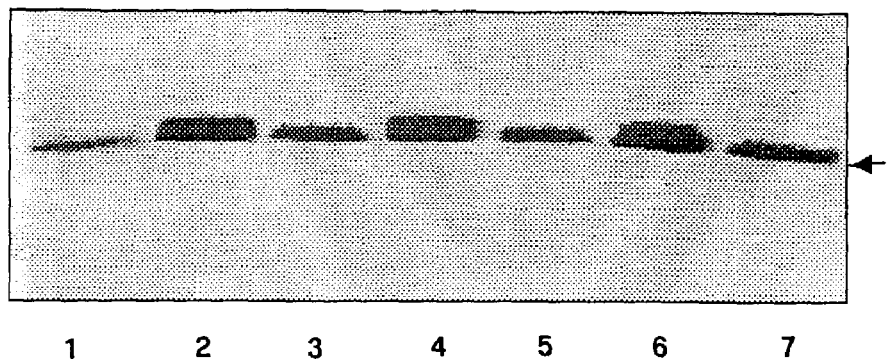

FIG. 14) Western blot analysis of cytosolic extracts from RCE cells with 1 μg/ml anti-cytochrome c mAb. Lanes: 1) untreated control; 2) UVC irradiation; 3) Coenzyme $Q_{10}$ treatment and UVC irradiation; 4) 200 μM Antimycin A; 5) Coenzyme $Q_{10}$ treatment and 200 μM Antimycin A; 6) 20 μM ceramide; 7) Coenzyme $Q_{10}$ treatment and 20 μM ceramide. The cytoplasmic cytochrome c (arrow) band density increased following apoptotic treatment of RCE cells (lanes 2,4,6) as compared to untreated controls (lane 1). Application of Coenzyme $Q_{10}$ prior to apoptotic stimuli significantly reduced band density (lanes 3,5,7).

Figure 15:
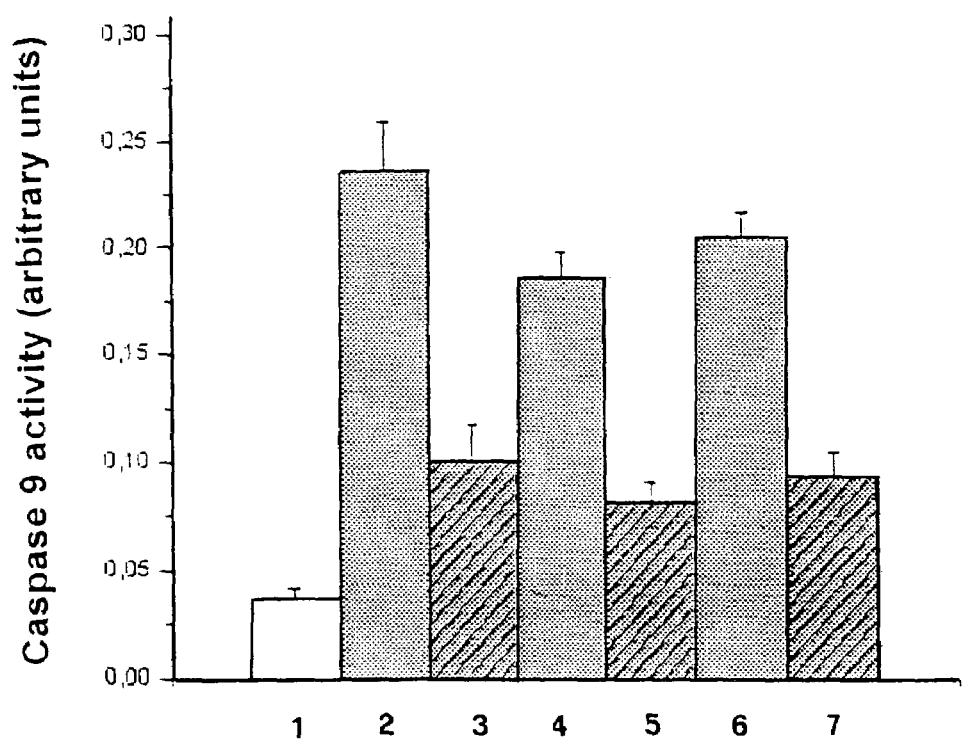

FIG. 15) Caspase 9 activity. Lanes: 1) untreated control; 2) UVC irradiation; 3) Coenzyme $Q_{10}$ treatment and UVC irradiation; 4) 200 μM Antimycin A; 5) Coenzyme $Q_{10}$ treatment and 200 μM Antimycin A; 6) 20 μM ceramide; 7) Coenzyme $Q_{10}$ treatment and 20 μM ceramide. Activity of caspase 9 increased by 6–8 fold following apoptotic treatment of RCE cells (lanes 2,4,6). Application with Coenzyme $Q_{10}$ significantly reduced caspase 9 activation in all cases (lanes 3,5,7).

Figure 16:
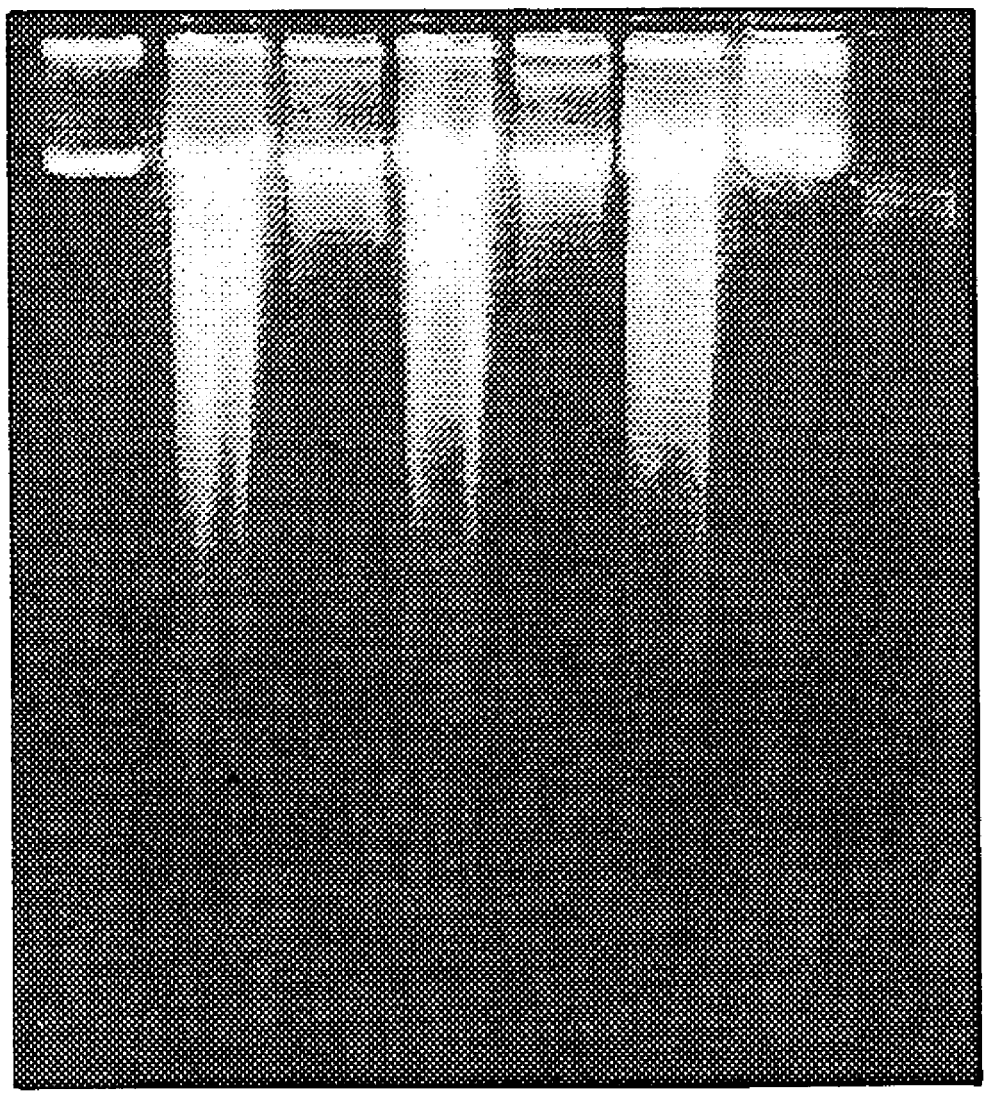

FIG. 16) Nucleosomal laddering. Lanes: 1) untreated control; 2) UVC irradiation; 3) Coenzyme $Q_{10}$ treatment and UVC irradiation; 4) 200 μM Antimycin A; 5) Coenzyme $Q_{10}$ treatment and 200 μM Antimycin A; 6) 20 μM ceramide; 7) Coenzyme $Q_{10}$ treatment and 20 μM ceramide. DNA fragmentation induced by all three apoptotic stimuli (lanes 2,4,6) was largely reduced when Coenzyme $Q_{10}$ treatment preceded apoptotic stimulus administration (lanes 3,5,7). M) DNA molecular weight marker λ/Hind III.

DESCRIPTION OF THE PREFERRED EMBODIMENTS

According to the present invention Coenzyme $Q_{10}$, or a functionally equivalent derivative thereof, can be used for the manufacture of a medicament for topic administration on the eye. Said medicament comprising the Coenzyme $Q_{10}$, or a functionally equivalent derivative thereof, preferably is in an eye drop form and can be the ophthalmic solution as described in PCT WO01/37851. The ophthalmic solution can be administered locally by superficial instillation.

Said composition comprises: Coenzyme Q10, or a functionally equivalent derivative thereof, by 0,01 up to 2,0% p/w; tocopherol by 0,005 up to 0,1% p/w; and a mixture including a modified castor oil and a block copolymer of hydrophilic ethylene oxide and lipophilic propylene oxide having a prevailing proportion of polyoxyethylene, an average molecular weight between 10.000 and 13.000 Dalton and a HLB value (hydrophile/lipophile equilibrium) higher than 15, in a quantity sufficient to solubilize said components in aqueous solution, generally between 10 and 15% p/w.

The mixture of these two surfactants (polyoxyethylene-polyoxypropylene) and a modified castor oil (poly-ethylene glycol glyceryl-triricinoleate) produces the full micellar solubilization of the components of the pharmaceutical form.

A particular example of the above-mentioned block copolymer is a commercial product called Lutrol F127.

The coenzyme $Q_{10}$, or functionally equivalent derivatives thereof, concentrations, which may be utilized for the formulation of ophthalmic solutions, are between 0.01 and 2.0% parts by weight (p/w); more preferably between 0.1 and 1.0% p/w, the ideal concentration as corneal "anti-haze" being understood by 0.2% p/w. The tocopherol concentrations in these preparations are generally between 0.005 and 0.1% p/w; more preferably between 0.01 and 0.5% p/w.

In a more particular way, a preferred composition comprises: Coenzyme $Q_{10}$, or functionally equivalent derivatives thereof, by about 0,2% p/w; tocopherol by 0,02 up to 0,04% p/w; and the mixture including polyethylene glycol glyceryl-triricinoleate and an ethylene oxide/propylene oxide block polymer having a proportion of polyoxyethylene by about 70%, an average molecular weight of about 12.000 Dalton and a 22 HLB value.

The ingredient to be necessarily added to the formulations is a product causing the solution to have the right osmolar value. The solution containing the active principle only, in fact, results hypotonic compared to the lachrymal fluid. Other ingredients that may be added are pH correctors (comprising salts forming a buffer in the solution), products with antiseptic properties, complexants and preservatives, antioxidants and synergizing agents.

By way of example some formulation embodiments are listed:

Formulation 1

Ingredients Concentration % p/w
Coenzyme $Q_{10}$,
or a functionally equivalent derivative thereof, 0.20
Tocopherol 0,04
Copolymer 10.00
Modified castor oil 5.00
NaCl 0.45
Benzalkonium chloride 0.01
Bidistilled water q. s. to 100.00

Formulation 2

Ingredients Concentration % p/w
Coenzyme $Q_{10}$,
or a functionally equivalent derivative thereof, 0,10
Tocopherol 0.02
Copolymer 15.00
Mannitol 2.50
Benzalkonium chloride 0,01
Bidistilled water q. s. to 100.00

Formulation 3

Ingredients Concentration % p/w
Coenzyme $Q_{10}$,
or a functionally equivalent derivative thereof,
0.20 Copolymer 10.00 NaCl 4.50
Benzalkonium chloride 0.01
Phosphate buffer Sorensen pH 7.4 quantum sufficit to 100.00

The topical administration on the eye can be performed also with an eye paste.

The Coenzyme $Q_{10}$ or a functionally equivalent derivative thereof, according to the present invention, can be administered also in combination with other suitable active principles known in the art as suitable for the treatment or the attenuation or prevention of the above-mentioned optical diseases.

In another embodiment of the present invention Coenzyme $Q_{10}$, or a functionally equivalent derivative thereof, can be administered systemically. Among the possible ways of systemic administration the oral administration as well as the parenteral administration of Coenzyme $Q_{10}$ or of its functionally equivalent derivative is envisaged. Although oral administration could be indicated for any kind of patient, it could be particularly useful when administration is to be performed to children or to animals for which the administration of eye drops could raise difficulties. All modes of oral administration of Coenzyme $Q_{10}$ known in the art are suitable for the present invention, the amount of Coenzyme $Q_{10}$, or a functionally equivalent derivative thereof, preferred is comprised between 40, and 400 mg per day, preferably between 50 and 250.

Compositions suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such compositions may be prepared by any suitable method of pharmacy that includes the step of bringing into association the active compound and a suitable carrier. Among possible modes of oral administration of Coenzyme $Q_{10}$ or a functionally equivalent derivative thereof, the liquid compositions described in U.S. Pat. No. 6,441,050 or the compositions disclosed in U.S. Pat. No. 6,403,116 are suitable for the use of Coenzyme $Q_{10}$ according to the present invention.

Another way of systemic administration of Coenzyme $Q_{10}$ according to the present invention is through injectable compositions, wherein the composition comprises Coenzyme $Q_{10}$ and suitable veterinary or pharmaceutical carriers as described in U.S. Patent Application No. 20020119936. Among the possible injection modes suitable for administration, the compositions can be administered through subconjuntival, subtenonia, episcleral, subcutaneous, intravenous or intravitreous injections. Said compositions comprise Coenzyme $Q_{10}$, sterile aqueous and non-aqueous injection solutions, suspensions and emulsions of the active compound, which preparations are preferably isotonic with the blood of the intended recipient. These preparations may contain anti-oxidants, surfactants, buffers, bacteriostats, solutes that render the compositions isotonic with the blood of the intended recipient, and other formulation components known in the art.

Experimental Results and Examples

In the present examples, the Antimycin A, $C_2$ Ceramide and serum starvation are used to demonstrate the anti-apoptotic effect of Coenzyme $Q_{10}$ in anti apoptotic events not related to an excess of free radicals. The choice of said substances is due to their mechanism of action.

1) Antimycin A is an organic poison which blocks the cellular respiration, therefore the cellular capability of producing energy, by binding the complex III of the mitochondrial respiratory chain. As a consequence of this, also if inside the cell there is oxygen available, the mitochondrion does not succeed in utilizing it and, therefore, stops forming ATP through oxidative phosphorilations. The phenomenon is indicated as chemical (or also histotoxical) hypoxia, that is, the impossibility of using oxygen due to the poisoning of the respiratory chain; said hypoxia is associated to other kinds of hypoxia (hypoxic, anaemic and ischemic) which are due to the lack of actually used oxygen in the cellular environment.

The chemical hypoxia induced by Antimycin A has been here used as an experimental model of cellular damage analogous to the ischemic damage, as above reminded, that is very frequent in the spontaneous pathology of retinal cells and independent from the formation of free radicals.

2) Ceramide-induced apoptosis is mainly a consequence of its ability to collapse mitochondrial $\Delta\Psi$ either by direct inhibition of mitochondrial respiratory chain complex III or by formation of large transmembrane channels that raise mitochondrial permeability. 3) Withdrawal of survival factors, achieved in cultured cells by serum starvation, can commit cells to apoptosis by different mechanisms, such as MAP kinase induction, ceramide release, COX-2 activation, whose common effect is triggering the mitochondrion-dependent apoptotic pathway.

The reactive oxygen species (ROS) generation in response to Antimycin A, $C_2$-ceramide and serum starvation (11) has also been reported in some experimental models. However, since ROS are key mediator of apoptosis, it is not easy to establish whether ROS increase following application of apoptotic stimuli is a cause or an effect of apoptosis execution. This point is crucial for the exclusion that Antimycin A, $C_2$-ceramide and serum starvation could directly induce free radical generation became a critical preliminary condition. This has been performed by quantifying free radical levels in RCE early, immediately after application of apoptotic stimuli, that means prior to commencement of apoptosis execution. The increase of MDA and SOD activity, observed at the $2^{nd}$ hour after UVC-irradiation but not after treatment with Antimycin A or $C_2$-ceramide or serum starvation confirmed that the three latter apoptotic stimuli did not generate free radicals.

By way of comparison, always in the same cell cultures, the ultraviolets were taken as a model of apoptotic insult due also to the excess of free radicals.

The protective effect of Coenzyme $Q_{10}$ against apoptosis in rabbit keratocytes (Rabbit Corneal Epithelial Cells transformed with SV40, also designated as RCE), was experimentally proved in cultures induced by antimycin A, ceramide, serum starvation and 254-nm UVC exposure. Apoptosis has been evaluated by means of early and late markers such as the analysis of the cytoplasm redox status (malondialdehyde assay), levels of adenosine triphosphate (ATP. caspase 9 activity, cytochrome c release from mitochondrion and DNA fragmentation assay).

The distribution of Coenzyme $Q_{10}$ at the choroid and retina level in rabbits has also been verified. To this purpose New Zealand White rabbits underwent an instillation (about 100 μl) of the collyrium described in PCT WO01/37851, in the name of the same Applicant of the present application, every minute for 15 minutes and were immediately sacrificed. The eyes were washed in physiologic solution and the retinas together with the choroid were explanted therefrom. The tissue was then homogenated and quantified by HPLC. The results of all the experiments performed demonstrating the surprising anti-apoptotic effects of coenzyme $Q_{10}$ are illustrated in the following examples.

EXAMPLES

Example 1

Protective Effect of Coenzyme $Q_{10}$ Against the Hystotoxic Hypoxia Effect

Figure 1:
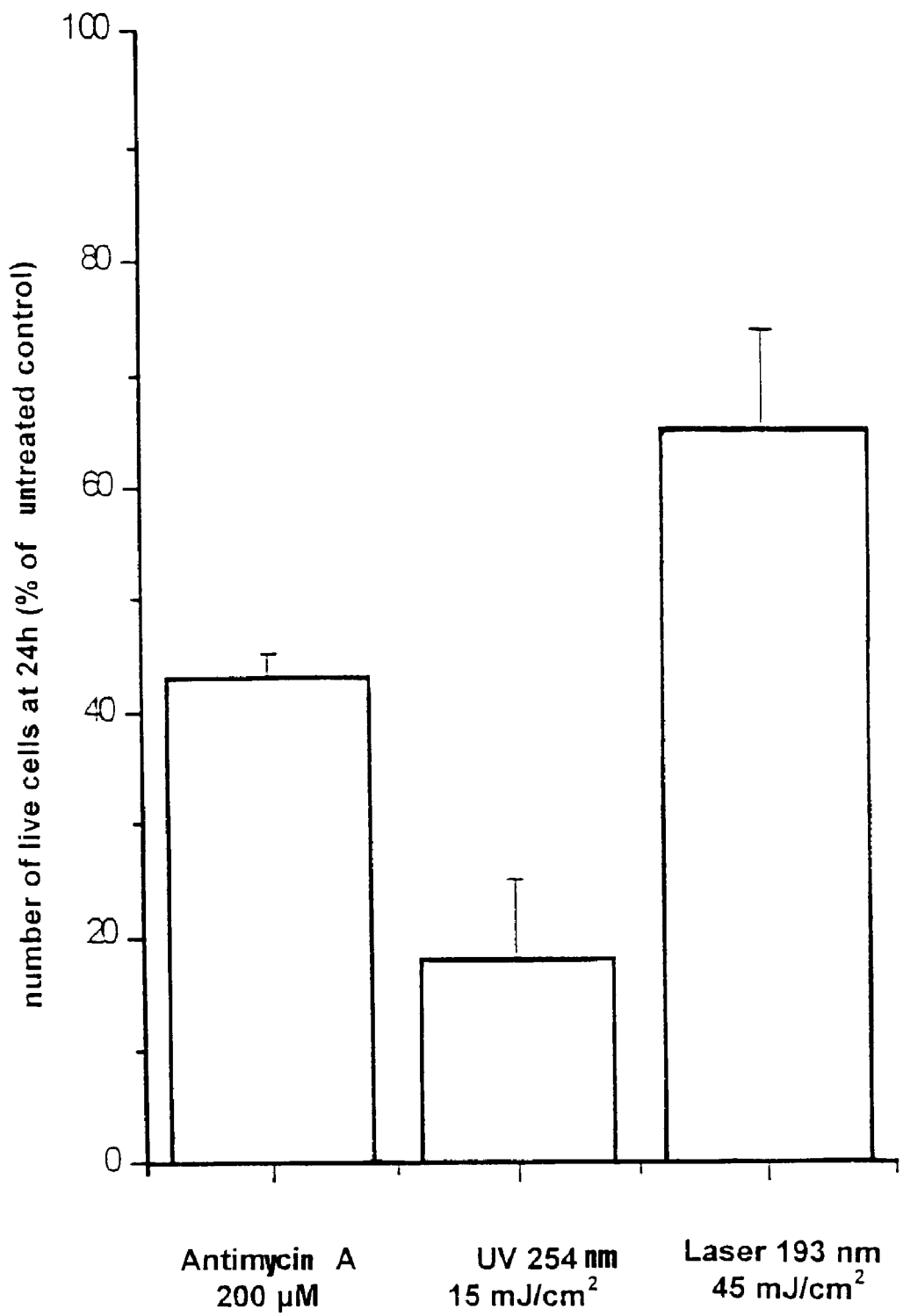
FIG. 1) represents a bar graph showing the number of living cells 24 hours after the treatment with UVC or Antimycin A compared to the not-treated control.

RCE cells were plated in thirty dishes the day before the administration of the apoptotic stimulus at the density of $2\times10^6$/Petri dish with 100-mm diameter. The day after, two series of 10 dishes each, were treated with antimycin A 200 μM and 254-nm UVC 15 J/m$^2$, respectively, whereas the third series was left untreated. After 24 hours the living cells were counted with the trypan blue method and shown on graph as control percentage (FIG. 1).

Figure 2:
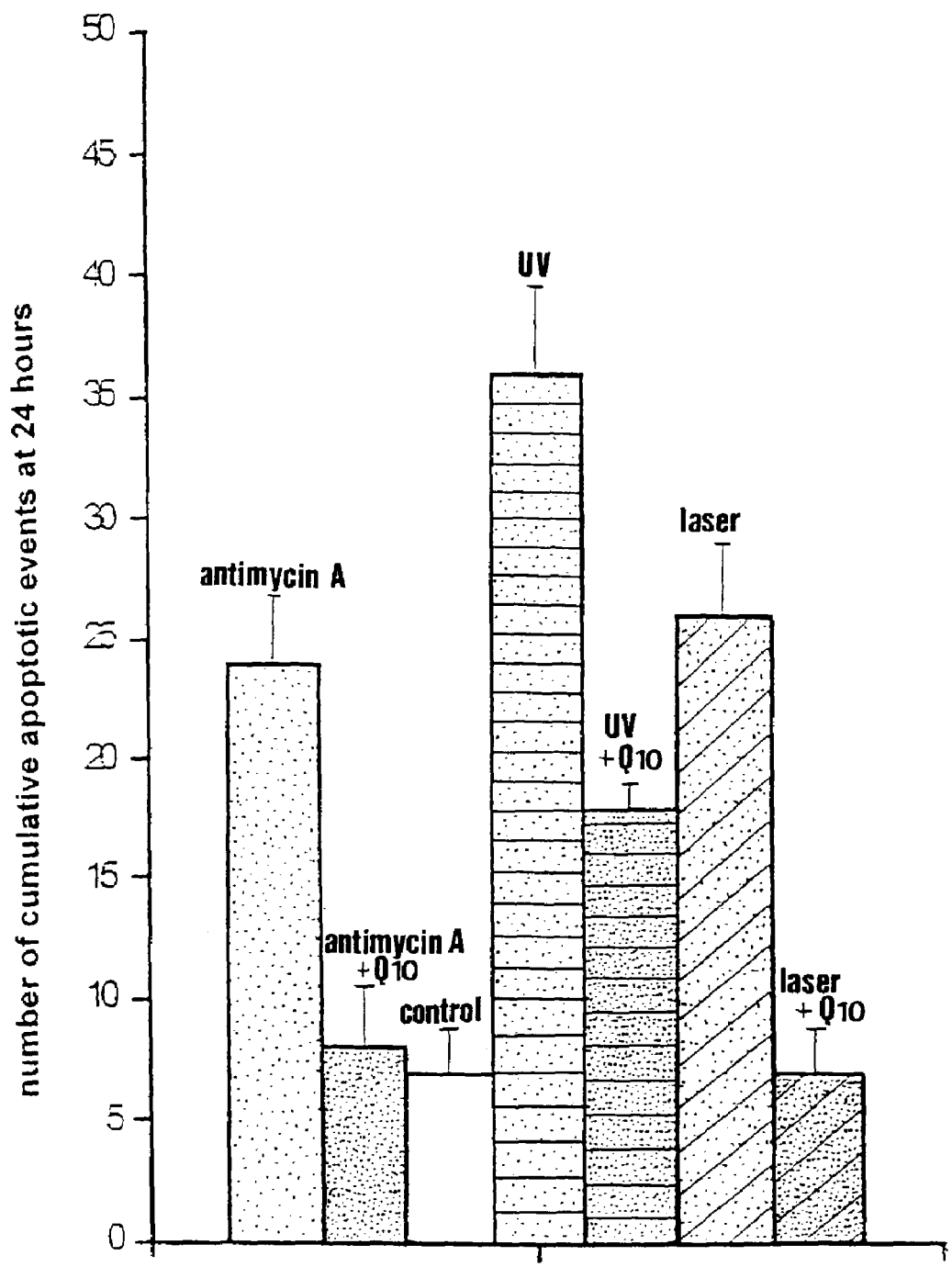
FIG. 2) represents a bar graph showing the protective effect of Coenzyme $Q_{10}$ against the apoptosis induced by UVC and antimycin A, 24 hours after treatment, expressed as number of total apoptotic events.

RCE cells were plated the day before the administration of the apoptotic stimulus at the density of $2\times10^6$/Petri dish with 100-mm diameter. The day after antimycin A at the concentration of 200 μM in combination with Coenzyme $Q_{10}$, 10 μM in Lutrol F127™ 0.04% or with only Lutrol F127™ 0.04% was added to one dish. From now on "treated with Coenzyme $Q_{10}$" refers to Coenzyme $Q_{10}$ vehiculated with Lutrol F127™ 0.04%, whereas the control is always meant as treated with Lutrol F127™ 0.04% only. Another dish was treated with 254-nm UVC 15 J/m$^2$ alone or in combination with Coenzyme $Q_{10}$ 10 μM. The cells were recorded by means of time-lapse video microscopy and the cumulative apoptotic events recorded after 24 hours were shown on graph vs. time (FIG. 2). The shown values represent the average of 5 experiments.

Example 2

Indirect Evaluation of the Production of Free Radicals Following Treatment with Antimycin A and 254-nm UVC by Measuring the Levels of Malondialdehyde and of the Efficiency of Coenzyme $Q_{10}$ in Preventing Said Production The malondialdehyde is a product of lipid peroxidation, which occurs following exposure of polyunsaturated fatty acids to free radicals. The production of malondialdehyde is then routinely assumed as production index of the radicals themselves by treatments with electromagnetic radiations or oxidant substances.

Coenzyme $Q_{10}$, as antioxidant, decreases the malondialdehyde production by indicating an action thereof, which inhibits the free radicals formation.

Figure 3:
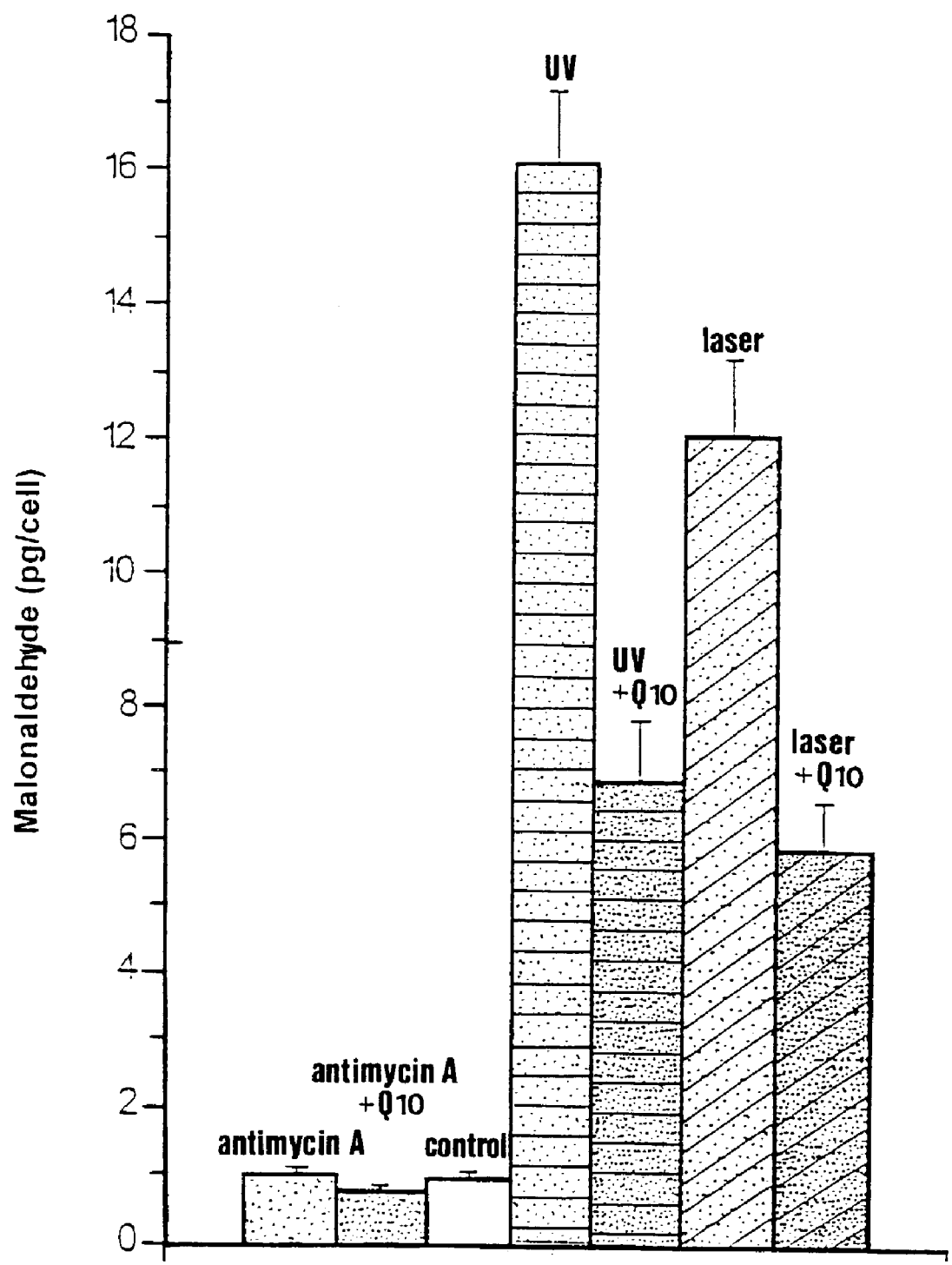
FIG. 3) represents a graph showing the effect of Coenzyme $Q_{10}$ on the malondialdehyde levels after treatment with UVC or antimycin A.

In order to perform the malondialdehyde assay, RCE cells were plated at the density of $5 \times 10^5$ cells/dish in 20 Petri dishes with 100-mm diameter and incubated overnight in 5% $CO_2$ atmosphere, 37° C. Subsequently, the dishes were preincubated for 2 hours with Coenzyme $Q_{10}$ (10 dishes), or left untreated (10 dishes), washed with 8 ml of physiological saline solution buffered with sterile phosphate (PBS), additioned with $Ca^{++}$ and $Mg^{++}$. The dishes were submitted to a treatment with antimycin A (200 µM) or 254-nm (15 J/cm$^2$) ultraviolet radiation as shown in FIG. 3. PBS was replaced by fresh medium additioned or not with Coenzyme $Q_{10}$ and the dishes were incubated for other 2 hours. Upon carrying out the assay, the cells were detached with trypsin according to standard procedures and counted by means of globule-counting chamber. The cells of the various samples were then lysed by adding thrichloracetic acid (TCA) and centrifuged for 20 minutes at 12,000 RPM in order to precipitate proteins.

To 300 µl of supernatant of each sample, 300 µl of thiobarbituric acid (TBA) by 1% were added. The mixtures were incubated at 95° C. for 30 minutes, centrifuged for 20 minutes at 12,000 RPM and the optic absorption of the supernatant resulting by spectrophotometric analysis at 532 nm was assessed.

The obtained values were compared with a calibration standard curve and normalized for the number of cells. In FIG. 3 the protective effect of Coenzyme $Q_{10}$ following treatment with antimycin A or UVC radiation is shown.

The assay then demonstrates, by direct comparison with other means of known art, the restraining action performed by Coenzyme $Q_{10}$ on the peroxidation level of the fatty acids by free radicals and indirectly the protective effect against free radicals themselves produced by UVC treatment. FIG. 3 also shows that the peroxidation level of fatty acids in case of treatment with antimycin A is similar to the one of the untreated control and this confirms the capability of Coenzyme $Q_{10}$ to protect against apoptosis independently from the free radicals scavenger property thereof emphasized in FIG. 2.

Example 3

Evaluation of Adenosine Triphosphate (ATP) Levels Following Treatment with Antimycin A and 254-nm UVC The ATP levels are strictly correlated to the cell death pattern, which occurs following biochemical damage. For example, an ATP level lower than 20% of the normal value is responsible for necrosis whereas the higher levels still enable the occurrence of apoptosis which is notoriously a process requiring energy.

Whereas it was ascertained that the ATP levels are drastically reduced following treatment with radiations, it resulted that, according to the present invention, Coenzyme $Q^{10}$ was able to prevent said reduction.

Figure 4:
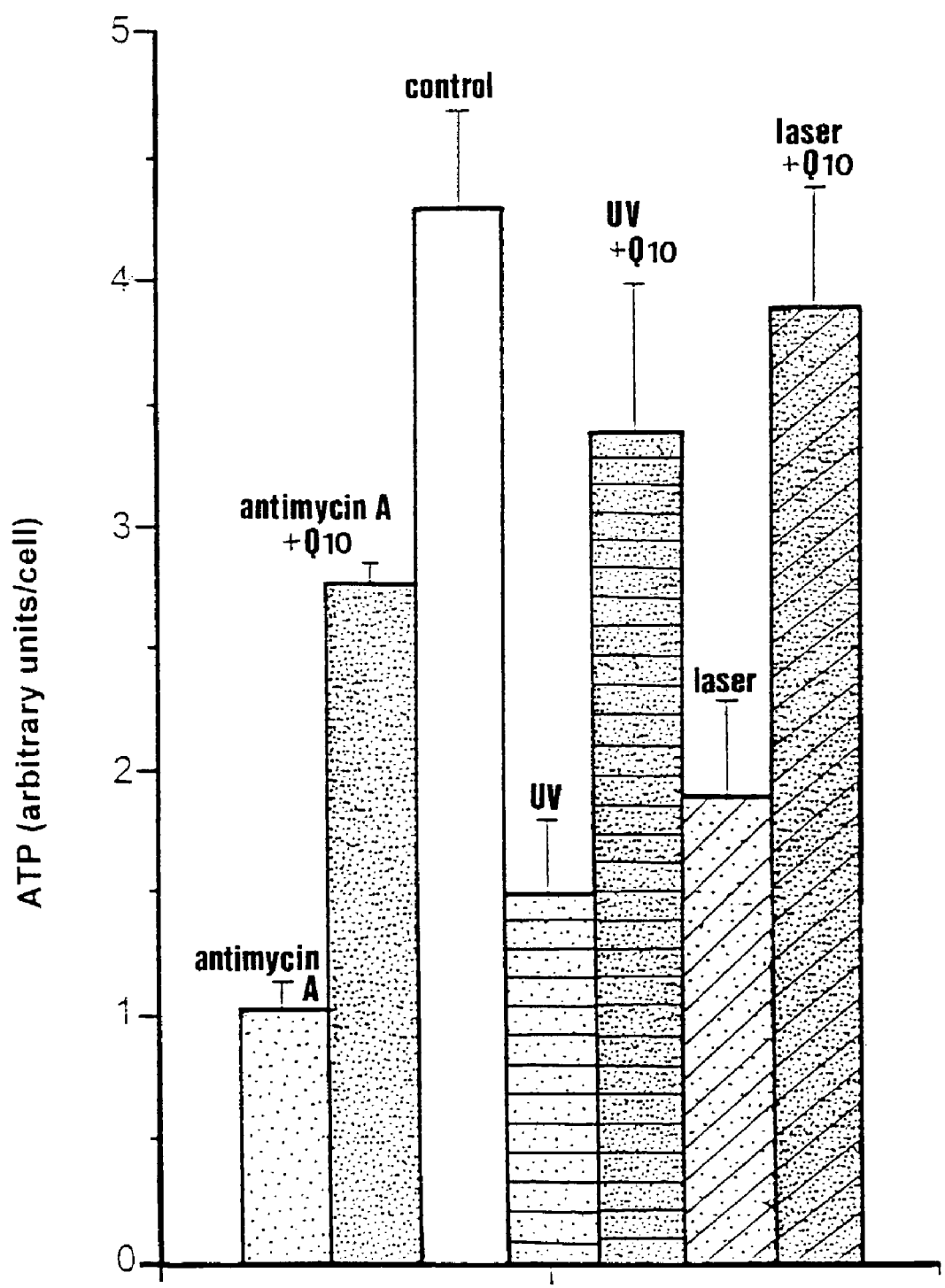
FIG. 4) represents a graph showing the effect of Coenzyme $Q_{10}$ on the adenosine triphosphate (ATP) levels after treatment with UVC and antimycin A.

In order to perform the ATP assay, RCE cells were plated at the density of $5 \times 10^5$ cells/dish in 10 Petri dishes of 10-cm diameter and incubated overnight in 5% $CO_2$ atmosphere, 37° C. Subsequently the dishes were preincubated for 2 hours with Coenzyme $Q_{10}$ at 10 µM or with the single vehicle. The medium was then replaced with 8 ml of sterile PBS, additioned with $Ca^{++}$ and $Mg^{++}$ and the dishes were treated with antimycin A (200 µM) or to 254-nm UVC (15 J/cm$^2$), as shown in FIG. 4. Subsequently the PBS was replaced with fresh medium additioned or not with Coenzyme $Q_{10}$ and the plates were incubated for other 2 hours. Upon carrying out the assay the cells were detached with trypsin according to standard procedures and counted by means of globule-counting chamber. The cells were then resuspended in distilled $H_2O$ at the concentration of $6 \times 10^4$ cells/L, immediately boiled for 5 minutes and frozen at -20° C. for subsequent analysis.

The ATP quantification in the extracts was performed by the "ATP Determination Kit" (Molecular Probes, USA) kit, based upon the firefly luciferase according to the supplier instructions. To detect fluorescence, an analyser for liquid scintillation (Camberra Packard, USA) preset for the bioluminescence analysis was utilized.

This assay quantitatively demonstrates the protective effect of Coenzyme $Q_{10}$ opposing the decrease in the ATP level produced by antimycin A and by UVC radiations.

Example 4

Localization of Coenzyme $Q_{10}$ at the Level of Choroid and Retina of New Zealand White Rabbits Administered Topically Treatment of Rabbits and Isolation of Choroid-Retinas The animals were sedated with an intramuscular injection of Zoletil (0,25 ml per Kg) and one of Rompun (0,15 ml per Kg) and anaesthetized with a gaseous mixture of oxygen, nitrogen monoxide and isofluorane and treated by instilling, for 15 minutes, 100 µl (2 drops) per minute the collyrium described in the PCT WO01/37851, in the name of the same Applicant, or the sole vehicle.

The animals were then sacrificed with an intracardiac injection of Tanax 82 (3 ml). Eyes were then explanted, washed with a physiological solution so as to eliminate blood and cleaned out of muscles and optic nerve. Cornea were then ablated with corneal scissors, the crystallines were eliminated, whereas the choroidsretinas together with sclera and vitreous humours were preserved at -80° C. until determination of the antioxidants.

Extraction and Chromatographic Determination of Antioxidants

The sample was homogenized with Turrax in 1 ml of bidistilled water and the liposoluble antioxidants (Coenzyme $Q_{10}$, retinol, α-tocopherol, β-carotene) were extracted by using 2 ml of extraction mixture (95% ethanol and 5% isopropanol) plus 5 ml hexane; the mixture was stirred for two minutes. The procedure produced the whole oxidation of the Coenzyme $Q_{10}$ possibly existing in a reduced form.

The sample was then centrifuged at room temperature at 3640 g for 10 min., the supernatant was recovered, evaporated to dryness and resuspended in ethanol.

Figure 5:
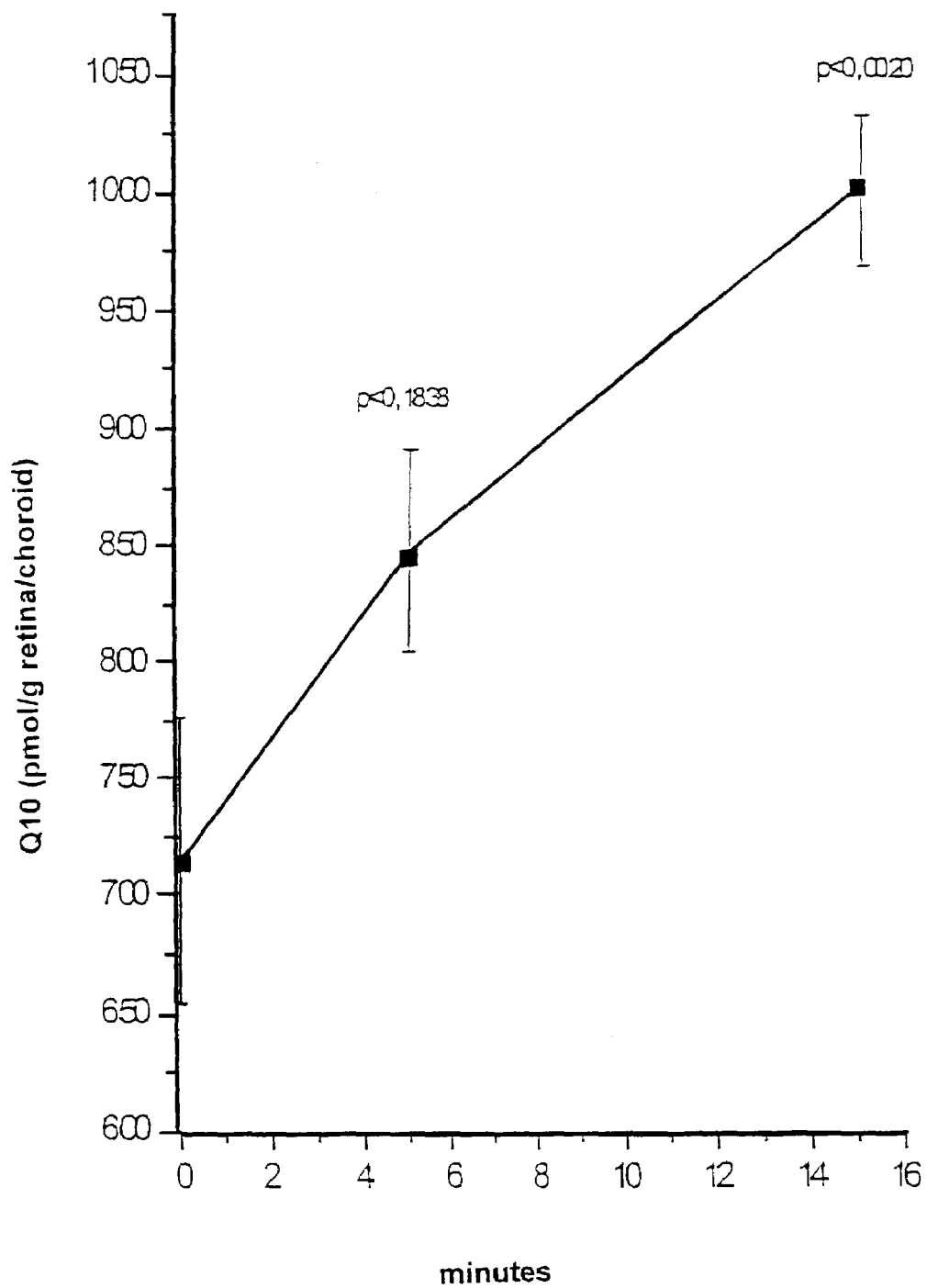
FIG. 5) represents a graph showing the captation kinetics of Coenzyme $Q_{10}$ by choroid/retina after treatments with a collyrium formulation, by New Zealand white rabbits, compared to the untreated control.
Figure 6:
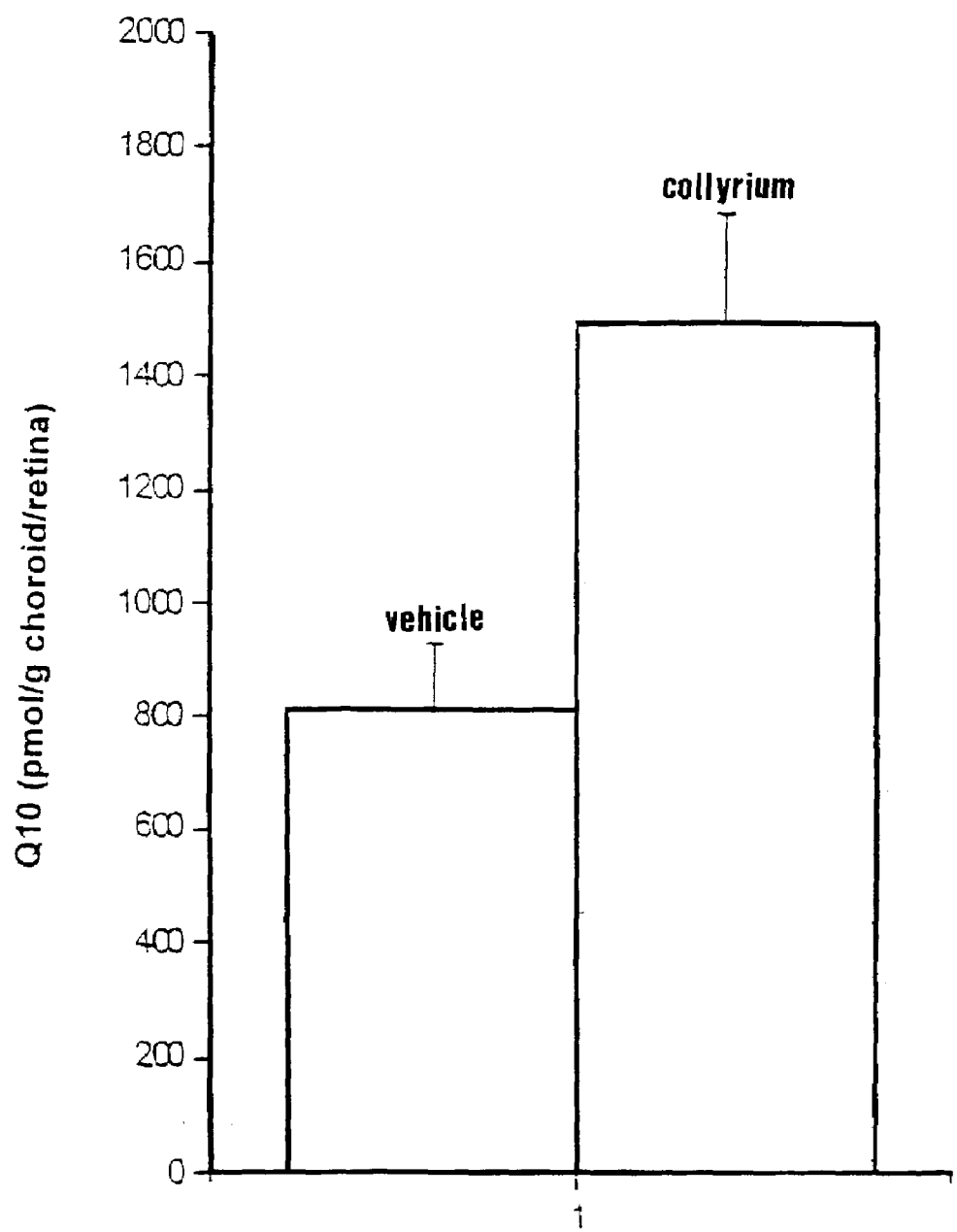
FIG. 6) represents a graph showing the captation of Coenzyme $Q_{10}$ by choroid/retina of New Zealand white rabbits treated with collyrium formulation, compared to the untreated control.
Figure 7A:
FIG. 7) Detection of DNA fragmentation in apoptotic nuclei by the Klenow Fragment End Labelling (FragEL, Oncogene Research Products) of DNA. RCE cells were stimulated with Antimycin A (A); Coenzyme $Q_{10}$ treated prior to stimulation with Antimycin A (B); serum-starved (C); Coenzyme $Q_{10}$ treated prior to serum starvation (D).
Figure 7B:
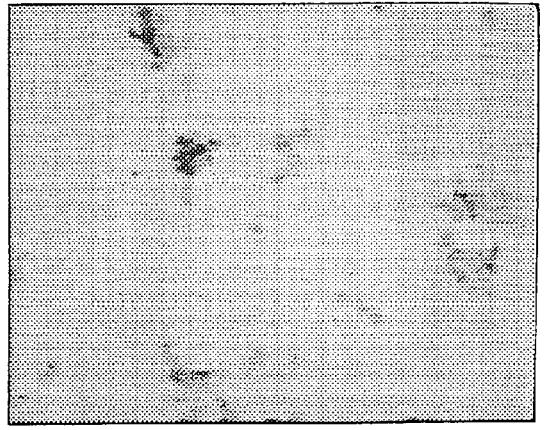
Figure 7C:
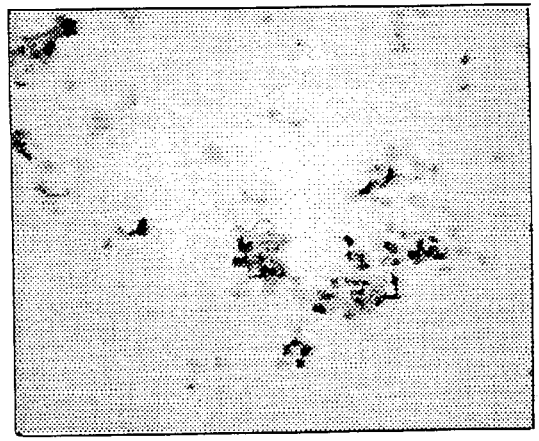
Figure 7D:
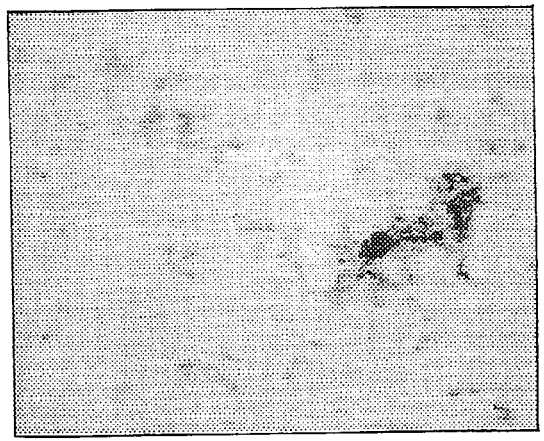

Antioxidants were separated by inverse phase HPLC, by using a column KROMASIL 100 Å-$C_{18}$ 250×4,6 mm having a precolumn of the same material, through a convex gradient (phase A: 90% methanol and 10% water; phase B: 50% methanol, 25% isopropanol and 25% hexane; elution speed: 1,5 ml/min.). The oxidized Coenzyme $Q_{10}$ was detected by means of a multidiode spectrophotometer at wavelengths of 275 nm. The quantitative determination was performed by referring to standard curves. The results, which show the uptake kinetics of Coenzyme $Q_{10}$ captured by choroid/retina cells and the presence of coenzyme $Q_{10}$ in said tissues, are shown in FIGS. 5 and 6, respectively.

Analogous data, showing the anti-apoptotic effect of Coenzyme $Q_{10}$, were obtained on mouse fibroblasts (RAT-1) and on human retinal cells (Human Retinal Pigmented Epithelia also designated as RPE).

Given the results obtained on the inhibition of apoptotic phenomena due to hypoxia by Coenzyme $Q_{10}$, the present invention claims the use of Coenzyme $Q_{10}$ (or ubiquinone $Q_{10}$ or Coenzyme $Q_{10}$), in the prevention, treatment and/or attenuation of the degenerative ocular pathologies deriving from apoptotic phenomena, i.e. programmed cell death (PCD) with the exclusion of the apoptotic phenomena due to excess of free radicals.

The topical administration is performed by using the collyrium described in the PCT WO01/37851, in the name of the same Applicant, whereas the administration by systemic way is performed orally, for example by administering a quantity of Coenzyme $Q_{10}$ higher than 20 mg/die, in particular in the range of 40 to 50 mg.

Example 5

Protective Effect of Coenzyme Q10 Against UVC Irradiation, Antimycin A, $C_2$-Ceramide and Serum Starvation Induced Apoptosis A rabbit corneal keratocytes (RCE) cell line was maintained in Dulbecco's Modified Eagle's Medium (DMEM), HAM's nutrient mixture F12 1:1, supplemented with 15% foetal bovine serum (FBS), 2 mM glutamine, 5 µg/ml insulin, 10 ng/ml EGF and 50 UI/ml penicillin, in humidified atmosphere of 5% $CO_2$ at 37C. Cells were plated at $3×10^5$/plate. Four damaging agents were applied at doses experimentally established to induce apoptosis: UVC irradiation (254 nm) at 15 mJ/cm$^2$, the respiratory chain blocker Antimycin A at 200 µM concentration, the apoptotic signalling lipid $C_2$-ceramide (a synthetic cell-permeable analogue of endogenous ceramides) at 20 µM concentration and FBS restriction to 0.5%. Treatments with 10 µM Coenzyme $Q_{10}$ dissolved in 0,04% Lutrol F107 used as vehicle to assure cellular uptake of this hydrophobic molecule or with 10 µM Vitamin C (ascorbic acid) was initiated two hours prior to application of apoptotic stimuli. Vehicle alone-treated cells were used as controls. The anti-apoptotic effects of Coenzyme $Q_{10}$ or Vitamin C against UVC irradiation, Antimycin A, $C_2$-ceramide and serum starvation were evaluated by light microscopy and ultramicroscopic. Identification of apoptotic cells with fragmented DNA was carried out by end labelling with the Klenow-FragEL™. In this assay, apoptotic cells are easily recognised by the presence of a dark brown staining in contrast to viable cells that, instead, appear green or even unstained. Significant number (30%–60%) of RCE cells examined at the $24^{th}$ hour following UVC irradiation, administration of Antimycin A or $C_2$-ceramide, and serum starvation contained brown-stained fragmented DNA. RCE cells treated with 10 µM Coenzyme $Q_{10}$ two hours before application of apoptotic stimuli stained green. Treatment with 10 µM Vitamin C prevented apoptosis only in response to UVC-irradiation. This indicated that treatment with Coenzyme $Q_{10}$ prevented apoptosis by a mechanism independent from its free radical scavenging property. Lack of protective effect by Vitamin C strongly supported this evidence. Results obtained with Antimycin A and serum starvation either in the absence (panels at left) or in the presence (panels at right) of Coenzyme $Q_{10}$ are shown in FIG. 7. In further experiments serum starvation as apoptotic stimulus and pre-treatment with Vitamin C were not included.

Figure 8A:
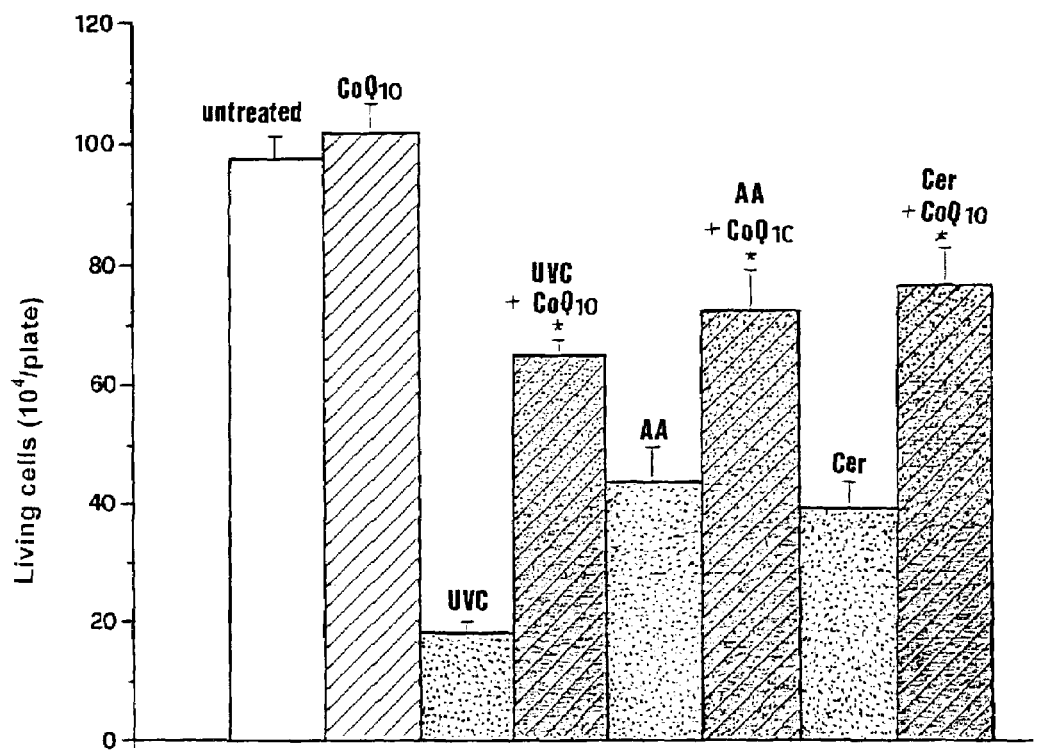
FIG. 8) RCE survival expressed as number of living cells/plate determined by MTT analysis 24 hours after UVC irradiation, administration of 200 μM Antimycin A; or 20 μM ceramide preceded or not by treatment with 10 μM Coenzyme $Q_{10}$ (FIG. 8A) or 10 μM Vitamin C (FIG. 8B). Cells were initially plated at 3×10$^5$ cells/plate. Each point is the mean±SE of 5 experiments for FIGS. 8A and 3 experiments for FIG. 8B. *p≦0.005 compared to Coenzyme $Q_{10}$ or Vitamin C untreated cells.
Figure 8B:
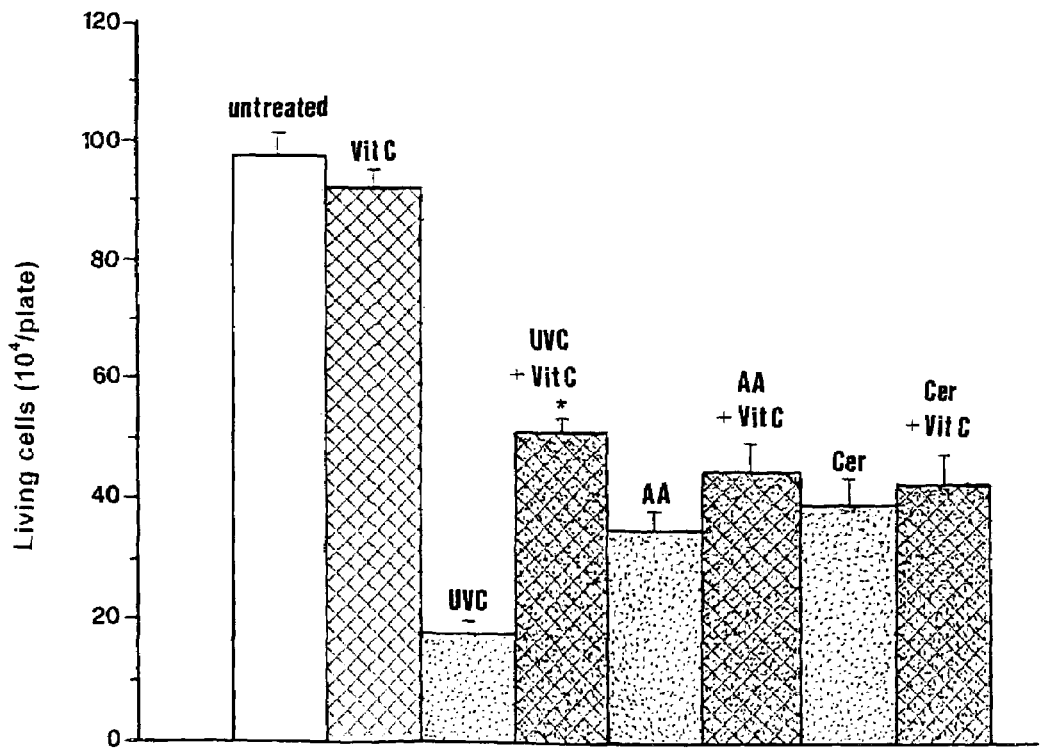
Figure 9A:
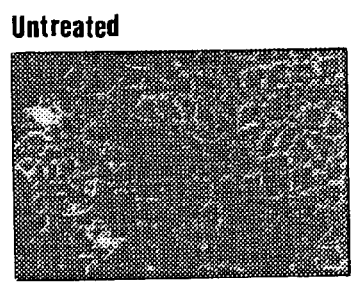
FIG. 9) Time-lapse videomicroscopy of RCE cells 24 hours after UVC irradiation (left panels); stimulation with 200 μM Antimycin A (central panels); or stimulation 20 μM ceramide (right panels), preceded or not by treatment with 10 μM Coenzyme $Q_{10}$. (A) Untreated RCE cells; (B) UVC irradiated; (C) treated with Coenzyme $Q_{10}$ prior to UVC irradiation; (D) stimulated with Antimycin A (AA); (E) treated with Coenzyme $Q_{10}$ prior to stimulation with Antimycin A; (F) stimulated with ceramide (G) treated with Coenzyme $Q_{10}$ prior to stimulation with ceramide. Apoptotic RCE cells appear as white, shrunken and detached from substrate. Their number is significantly reduced after treatment with Coenzyme $Q_{10}$ (bottom panels).
Figure 9B:
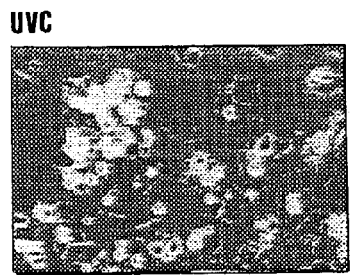
Figure 9C:
Figure 9D:
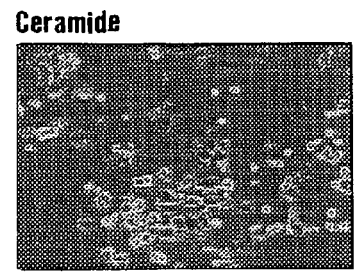
Figure 9E:
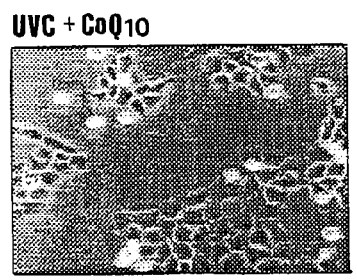
Figure 9F:
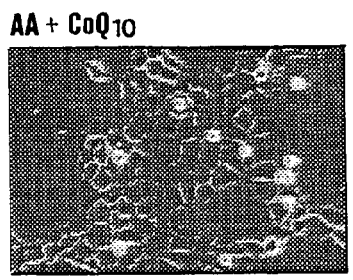
Figure 9G:
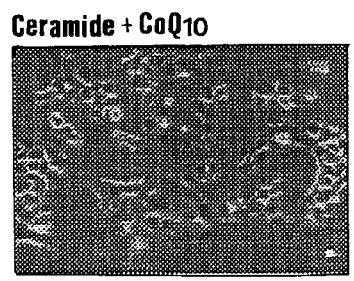
Figure 10A:
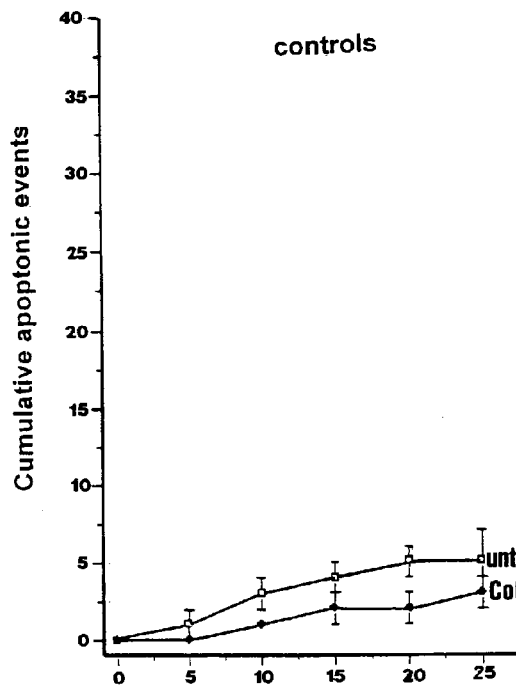
FIG. 10) Reduction of cumulative apoptotic events by treatment with Coenzyme $Q_{10}$ in RCE cells. Apoptotic events were scored by Time-lapse video microscopy during 24 hours after apoptotic stimuli as previously described. With respect to untreated cells, UVC irradiation, Antimycin A and ceramide increased markedly the number of cumulative apoptotic events in RCE cells, which was significantly reduced by treatment with the Coenzyme $Q_{10}$.
Figure 10B:
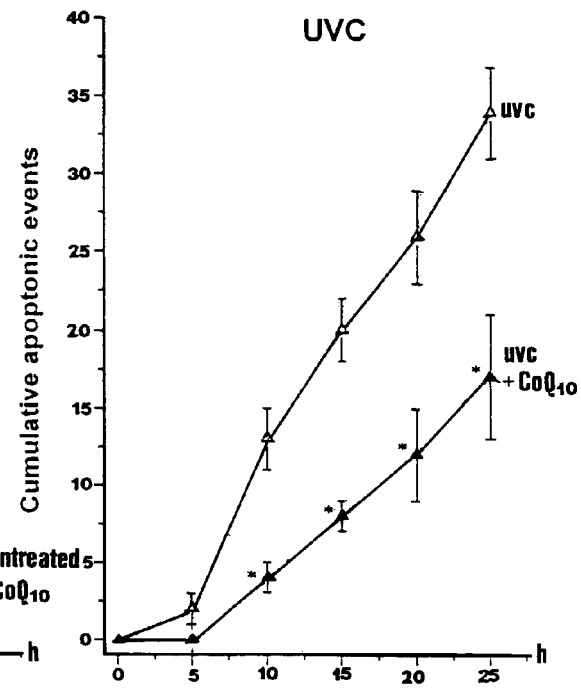
Figure 10C:
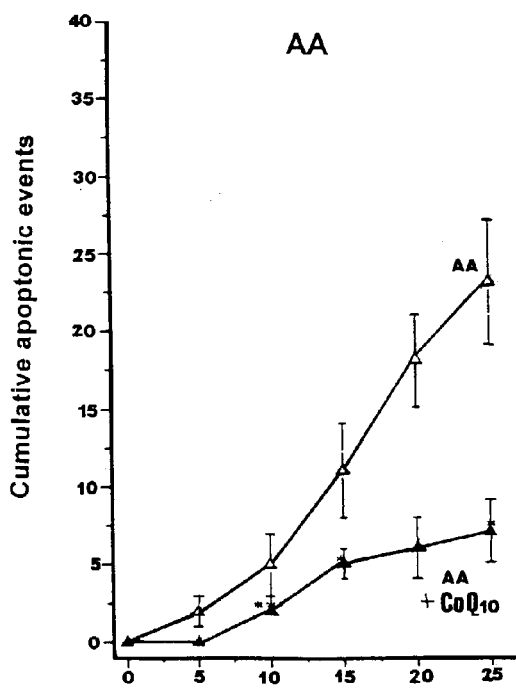
Figure 10D:
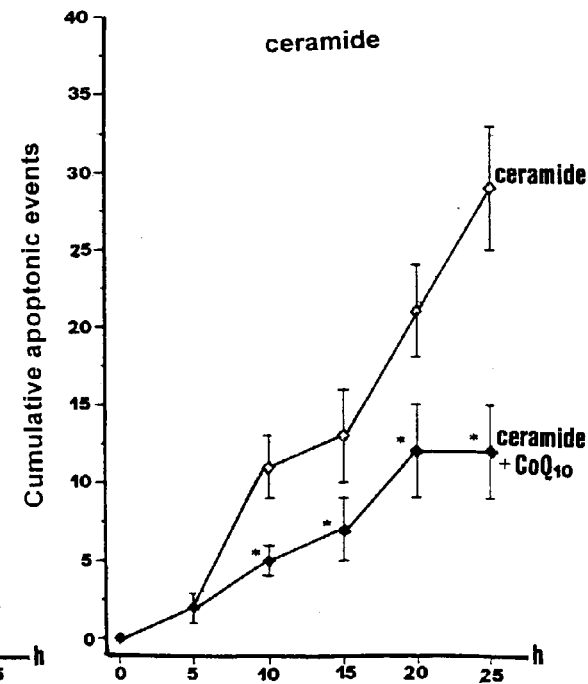

The number of living cells following above described treatments and analysed by MTT assay was then evaluated (FIG. 8). As shown in FIG. 8A, UVC irradiation, Antimycin A and $C_2$-ceramide decreased by 82%, 56% and 61%, respectively, the number of living cells. In all cases, treatment with Coenzyme $Q_{10}$ 10 µM protected RCE cells, which resulted in number of living cells decreased by only 49%, 29% and 24%, respectively. On the contrary (FIG. 8B), treatment with Vitamin C, used as pure free radical-scavenger, effectively protected RCE cells from apoptosis only in response to UVC-irradiation. FIG. 9 shows the Time-lapse Video microscopy aspects of RCE keratocytes cultured for 24 hours in the absence of any treatment (upper panel) or following either UVC irradiation (left) or treatment with Antimycin A (center) or $C_2$-ceramide (right), preceded or not by a 2-hour treatment with Coenzyme $Q_{10}$. Following all three treatments a high number of RCE cells underwent apoptosis, but treatment with Coenzyme $Q_{10}$ dramatically decreased this number, indicating the effectiveness of Coenzyme $Q_{10}$ in apoptosis prevention against any apoptotic stimulus. Corresponding quantitative data are reported in FIG. 10. With respect to untreated or Coenzyme $Q_{10}$ treated controls the number of cumulative apoptotic events scored by Time-lapse video microscopy markedly increased following application of all three apoptotic stimuli, but to significantly lower extent if the cells were treated with the Coenzyme $Q_{10}$ for 2 hours before the induction of apoptosis.

Example 6

UVC Irradiation but not Antimycin A, C2-Ceramide and Serum Starvation Increases Free Radicals The effects of the UVC irradiation, Antimycin A, $C_2$-ceramide and serum starvation on free radical generation two hours after application of the stimuli, were analysed using malonaldeide level and SOD activity as indirect parameters. Cells were pre-treated or not with Coenzyme $Q_{10}$ or Vitamin C as described in Example 4. As shown in FIG. 11, substantial increases of MDA level (upper panel) and SOD activity (lower panel) with respect to untreated cells were obtained only in response to UVC irradiation (from 1.5 pg/cell to 16.5 pg/cell, and from 6.5 U/mg of protein to 19.5 U/mg of protein, respectively). Pre-treatment with Coenzyme $Q_{10}$ or Vitamin C reduced this increase.

Example 7

Coenzyme $Q_{10}$ Lowered ATP Levels in Response to Free Radical Unrelated Apoptotic Stimuli Execution of apoptotic death program requires massive consumption of ATP and, consequently, is accompanied by dramatic reduction of ATP cellular levels. Cells were treated as in Example 5. As shown in FIG. 12, UVC irradiation, Antimycin A and $C_2$-ceramide lowered ATP levels in RCE cells by 65%, 76%, and 81%, respectively, as compared to untreated controls. Administration of Coenzyme $Q_{10}$ significantly protected RCE cells against reduction of ATP levels. Indeed, in treated RCE cells the levels of ATP were reduced by 28% in UVC irradiated cells, by 41% in Antimycin A treated cells and by 51% in $C_2$-ceramide treated cells as compared to Coenzyme $Q_{10}$ treated only controls.

Example 8

Coenzyme $Q_{10}$ Counteracted Mitochondrial $\Delta\Psi$ Collapse, Cytochrome c Release, Caspase 9 Activation and DNA Fragmentation Elicited by Free Radical Unrelated Apoptotic Stimuli Cells were treated as in Example 5.

Detection of Change in Mitochondrial Transmembrane Potential ($\Delta\Psi$).

The change in mitochondrial transmembrane potential ($\Delta\Psi$) occurring during apoptosis was detected by fluorescence-based assay in RCE cells. The cells were cultured on cover slips, in DMEM medium containing the lipophilic cationic probe 5,5',6,6'-tetrachloro-1,1'3,3'-tetraethylbenzimidazol-carbocyanine iodide (JC-1, 5 mg/ml) (JC-1, Molecular Probes Inc. Eugene, Oreg., USA) for 15 min at 37° C. This dye has a unique feature: at hyperpolarized membrane potentials (to −140 mV) it forms a red fluorescent J-aggregate, whereas at depolarised membrane potentials (to −100 mV) it remains in the green fluorescent monomeric form. Prior to detection cells were washed in PBS and placed in an open slide flow loading chamber that was mounted on the stage of a confocal BioRad MRC 1024 ES scanning microscope (BioRad Laboratories Inc., Hercules, Calif., USA) equipped with a krypton/argon laser source. The fluorescence was monitored by using 488 and 568 nm wavelengths and collecting the emitted fluorescence with a Nikon plan Apo x60 oil-immersion objective. As shown in FIG. 13 UVC irradiation as well as treatments with Antimycin A or $C_2$-ceramide determined $\Delta\Psi$ collapse, in fact there was a shift in membrane charge observed as disappearance of fluorescent red-orange stained mitochondria and an increase in fluorescent green stained mitochondria.

Western Blot Analysis of Cytoplasmic Cytochrome c.

RCE cells were evaluated 24 hours following apoptotic stimuli. Cytosolic fractions were prepared as described in Ruties et al. 1999, J. Biol. Chem. 274, 24799–24807. Proteins in the cytosolic extracts were quantified by the BCA Protein Assay Reagent (PIERCE, Rockford, Ill., USA). Proteins (25 pg/lane) were electrophoresed through SDS polyacrylamide 12,5% gel, and electroblotted onto nitrocellulose membrane (Schleicher & Schuell, Keene, N.H.) using transblotter (BioRad Laboratories Inc., Hercules, Calif., USA). The non-specific signals were blocked with blocking buffer (5% w/v instant non fat milk powder in PBS) and incubated overnight at 4° C. with 1 µg/ml of anti-Cytochrome c monoclonal antibody (BD Pharmingen, San Diego, Calif., USA). The membrane was washed and subsequently incubated with goat anti-mouse IgG horseradish peroxidase conjugated (Sigma-Aldrich, Milan, Italy). Detection was carried out using a commercial chemo luminescence procedure (ECL, Amersham Pharmacia Biotech Europe, Freiburg, Germany). As shown in FIG. 14, 24 hours following induction of apoptosis, RCE cells showed an increase in cytoplasmic cytochrome c when compared to untreated RCE cells. When the treatments were preceded by the $CoQ_{10}$ administration, the cytoplasmic cytochrome c remained at similar levels to non-induced cells.

Analysis of Caspase 9 Activity.

Caspase 9 activity was determined by the Caspase-9 Colorimetric Protease Assay (BioSource Europe, S.A., Nivelles, Belgium). Cytosolic extracts, prepared by lysing cells with Cell Lysis Buffer provided in the kit, were incubated with the calorimetric substrate LEHD (Leu-Glu-His-Asp) conjugated to the chromophore p-nitroanilide (pNA), in 50 µl of 2× Reaction Buffer containing 10 mM DTT. After a 2-hour incubation at 37° C., the OD of samples was measured at 405 nm in BioRad ELISA reader. FIG. 15 shows a 6 to 8 fold enhancement of caspase 9 activity in RCE cells 24 hours after administration of apoptotic stimuli. When the stimulations were preceded by Coenzyme $Q_{10}$ administration the caspase 9 activity remained significantly lower, but not at the same levels as in non-stimulated RCE cells.

Mitochondrial transmembrane potential ($\Delta\Psi$) collapse, cytoplasmic cytochrome c, and caspase 9 activation are part of the intrinsic (mitochondrion-dependent) apoptotic pathway triggered by PTP opening. Pre-treatment with Coenzyme $Q_{10}$ largely prevented all these events. These results clearly indicated that, independently from its free-radical scavenging property, Coenzyme $Q_{10}$ prevented apoptosis execution by directly maintaining mitochondrial PTP in the closed conformation.

Analysis of DNA (Nucleosomal Laddering).

Apoptotic internucleosomal DNA fragmentation was evaluated by classical assay, detecting electrophoretically separated ladder of fragmented DNA. The genomic DNA was extracted from RCE cells as described by Blankenberg et al 1997, Blood 89, 3778–3786. The fragments were separated by gel electrophoresis in 0.8% agarose containing ethidium bromide (0.2 µg/ml), UV-visualized and photographed. Pre-treatment with Coenzyme $Q_{10}$ also prevented DNA internucleosomal fragmentation (FIG. 16) elicited by all apoptotic stimuli, which indicated that blocking of intrinsic apoptotic pathway by pretreatment with Coenzyme $Q_{10}$ suffices to prevent the "ignition" of entire apoptotic machinery triggered by apoptotic stimuli.

The invention claimed is:

1. A method for the treatment or attenuation of apoptotic events occurring in neurodegenerative pathologies of the posterior part of the eye, comprising administering topically onto the anterior part of the eye to a human or an animal a therapeutically amount of coenzyme $Q_{10}$ or ubiquinol, effective to treat said pathologies.

2. The method according to claim 1, wherein said neurodegenerative pathologies comprise heredofamilial, inflammatory, dysmetabolic, and senile age-related pathologies.

3. The method according to claim 2, wherein said neurodegenerative pathology is glaucoma.

4. The method according to claim 2, wherein said neurodegenerative pathology is the age-related macular degeneration.

5. The method according to claim 2, wherein said neurodegenerative pathology is retinitis pigmentosa.

6. The method according to claim 2, wherein said neurodegenerative pathology is Stargardt disease.

7. The method according to claim 2, wherein said neurodegenerative pathology is vitelliform macula cysts.

8. The method according to claim 2, wherein said neurodegenerative pathology is the cones dystrophy.

9. The method according to claim 2, wherein said neurodegenerative pathology is exudative or proliferating diabetic retinopathy.

10. The method according to claim 2, wherein said neurodegenerative pathologies comprise Hypertensive retinopathy, detachment of retina, retinoblastoma.

11. A method according to claim 1 for the treatment or attenuation of neurodegenerative pathologies of the posterior part of the eye, comprising administering topically onto the anterior part of the eye a composition including Coenzyme $Q_{10}$ or ubiquinol as an active principle for the treatment or attenuation of said neurodegenerative pathologies, wherein said composition comprises:

0.01 to 2.0% p/w Coenzyme Q10 or ubiquinol; 0.005 to 0.1% p/w tocopherol; and an amount of a mixture sufficient to solubilize said components coenzyme $Q_{10}$ or ubiquinol in an aqueous solution, said mixture including:

a modified castor oil and a block copolymer of hydrophilic ethylene oxide and a lipophilic propylene oxide having a prevailing proportion of polyoxyethylene, an average molecular weight between 10000 and 13000 Dalton and a hydrophile/lipophile equilibrium (HLB) value higher than 15.

12. A method according to claim 11, wherein said amount sufficient to solubilize said components in an aqueous solution is 10 to 15% p/w.

13. A method according to claim 11 or 12, wherein said modified castor oil is poly-ethylene glycol glyceryl-triricinoleate.

* * * * *